United States Patent
Kishida et al.

(10) Patent No.: US 8,550,710 B2
(45) Date of Patent: Oct. 8, 2013

(54) SAMPLE CELL FOR FLUORESCENT X-RAY ANALYSIS AND SAMPLE CELL ASSEMBLY INSTRUMENT

(75) Inventors: Mayuko Kishida, Kyoto (JP); Shintaro Komatani, Kyoto (JP); Sumito Ohzawa, Kyoto (JP); Takuji Kurozumi, Kyoto (JP); Satoru Goto, Kyoto (JP); Takashi Kinba, Kyoto (JP); Kimihiko Arimoto, Kyoto (JP)

(73) Assignee: Horiba, Ltd., Kyoto (JP)

( * ) Notice: Subject to any disclaimer, the term of this patent is extended or adjusted under 35 U.S.C. 154(b) by 288 days.

(21) Appl. No.: 12/900,171

(22) Filed: Oct. 7, 2010

(65) Prior Publication Data

US 2011/0085638 A1 Apr. 14, 2011

(30) Foreign Application Priority Data

Oct. 9, 2009 (JP) ................................. 2009-235383
Dec. 3, 2009 (JP) ................................. 2009-275671

(51) Int. Cl.
*G01N 23/223* (2006.01)
*B65D 6/00* (2006.01)
*B65D 8/14* (2006.01)

(52) U.S. Cl.
USPC ................. 378/208; 378/44; 378/45; 378/46; 378/47; 220/8; 73/864.91

(58) Field of Classification Search
USPC .............. 378/44–50, 208; 220/8; 73/864.91; 422/400, 547, 557
See application file for complete search history.

(56) References Cited

U.S. PATENT DOCUMENTS

| | | | | |
|---|---|---|---|---|
| 4,037,109 A * | 7/1977 | Hosokawa et al. | ............. | 378/45 |
| 4,448,311 A * | 5/1984 | Houser | ......................... | 206/527 |
| 4,587,666 A * | 5/1986 | Torrisi et al. | .................... | 378/47 |
| 4,643,033 A * | 2/1987 | Solazzi | .................... | 73/864.91 |
| 4,698,210 A * | 10/1987 | Solazzi | ....................... | 356/246 |
| 5,253,280 A * | 10/1993 | Mizuta | ............... | 378/45 |
| 5,451,375 A * | 9/1995 | Solazzi | ......................... | 422/549 |
| 5,454,020 A * | 9/1995 | Solazzi | ........................ | 378/45 |
| 5,630,989 A * | 5/1997 | Solazzi | ........................ | 422/557 |
| 5,981,292 A * | 11/1999 | Obenauf, Jr. | .................. | 436/175 |
| 6,009,766 A * | 1/2000 | Solazzi | ..................... | 73/864.91 |
| 6,012,325 A * | 1/2000 | Ma | ............................... | 73/24.02 |
| 6,428,751 B1 * | 8/2002 | Solazzi | ........................ | 422/557 |
| 6,603,544 B1 * | 8/2003 | Eckert | ........................... | 356/246 |
| 7,654,402 B2 * | 2/2010 | Kusuma et al. | ................... | 220/8 |

(Continued)

FOREIGN PATENT DOCUMENTS

| JP | 60-23719 | 7/1985 |
|---|---|---|
| JP | 64-083140 | 3/1989 |

(Continued)

*Primary Examiner* — Allen C. Ho

(57) ABSTRACT

In a sample cell that is sealed with an X-ray transmission sheet after a sample such as a liquid fuel or the like is contained therein, when an internal pressure is increased, a cup end surface is deformed so as to increase an internal capacity of the sample cell before the X-ray transmission sheet serving as a window part is expanded. The cup end surface is formed by folding a film-like material and, when the internal pressure of the sample cell is increased, the cup end surface is unfolded outwardly of the sample cell to increase the internal capacity of the sample cell. The increase in pressure is relieved by the increase in capacity, and the expansion of the X-ray transmission sheet is thereby prevented.

4 Claims, 35 Drawing Sheets

(56) References Cited

U.S. PATENT DOCUMENTS

| | | | |
|---|---|---|---|
| 7,722,821 B2 * | 5/2010 | Solazzi | 73/864.91 |
| 7,729,471 B2 * | 6/2010 | Burdett et al. | 378/47 |
| 7,981,380 B2 * | 7/2011 | Solazzi | 422/400 |
| 8,043,862 B2 * | 10/2011 | Solazzi | 422/547 |
| 8,404,197 B2 * | 3/2013 | Solazzi | 422/400 |
| 2005/0127073 A1 | 6/2005 | Kusuma et al. | |
| 2005/0127074 A1 | 6/2005 | Kusuma et al. | |

FOREIGN PATENT DOCUMENTS

| | | |
|---|---|---|
| JP | 02-285240 | 11/1990 |
| JP | 07-134082 | 5/1995 |
| JP | 09-127028 | 5/1997 |
| JP | 09-257674 | 10/1997 |
| JP | 2000-266705 | 9/2000 |
| JP | 3929460 | 6/2007 |
| WO | 2009/067498 | 5/2009 |

* cited by examiner

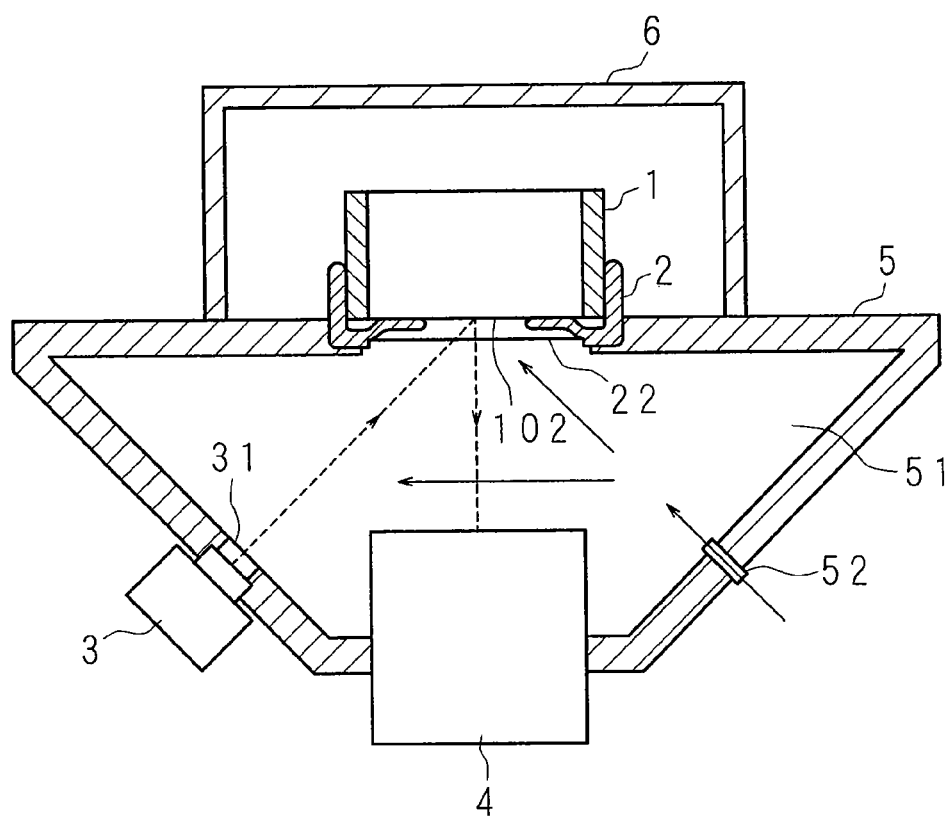
F I G. 1

F I G. 1 0 A
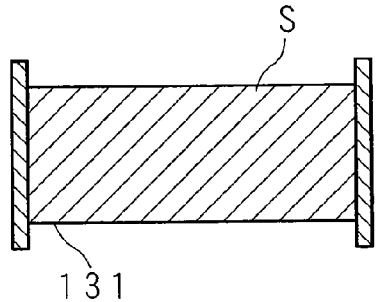
F I G. 1 0 B
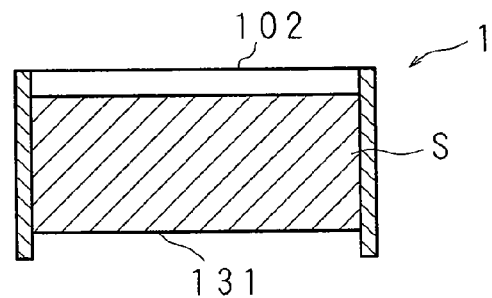
F I G. 1 0 C
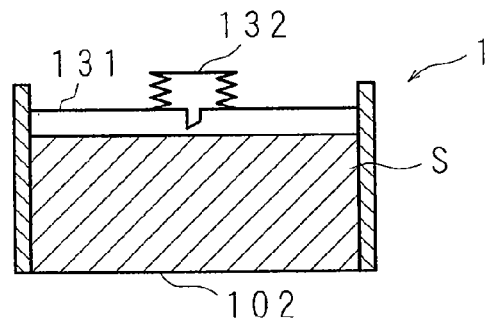
F I G. 1 0 D
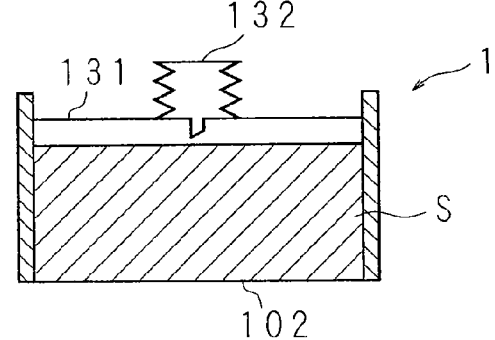

F I G. 1 3 A
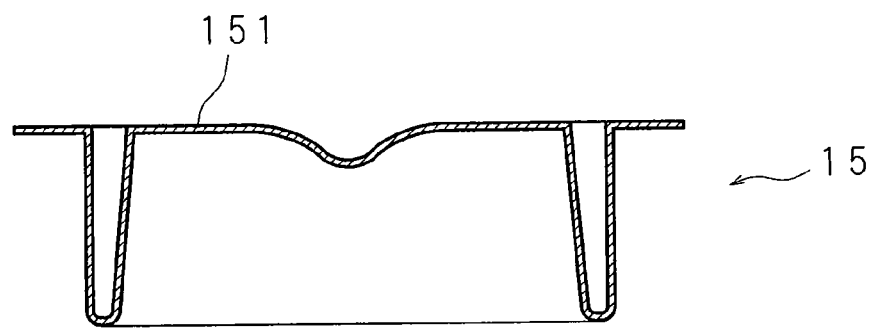
F I G. 1 3 B
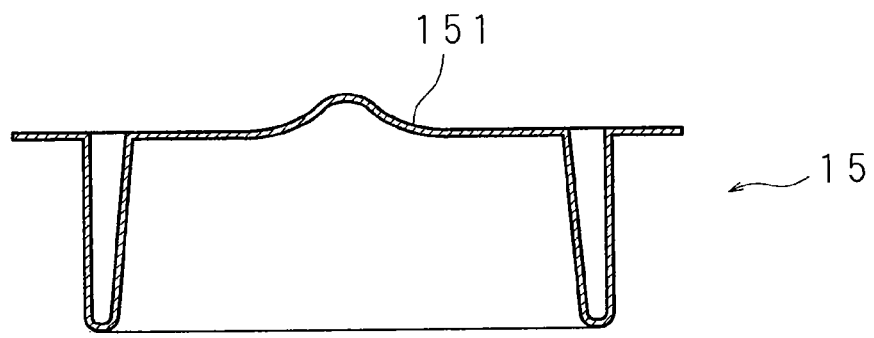

F I G. 1 5 A
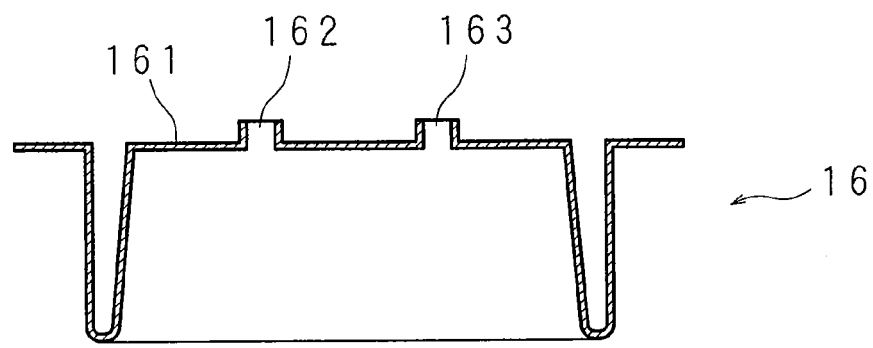
F I G. 1 5 B
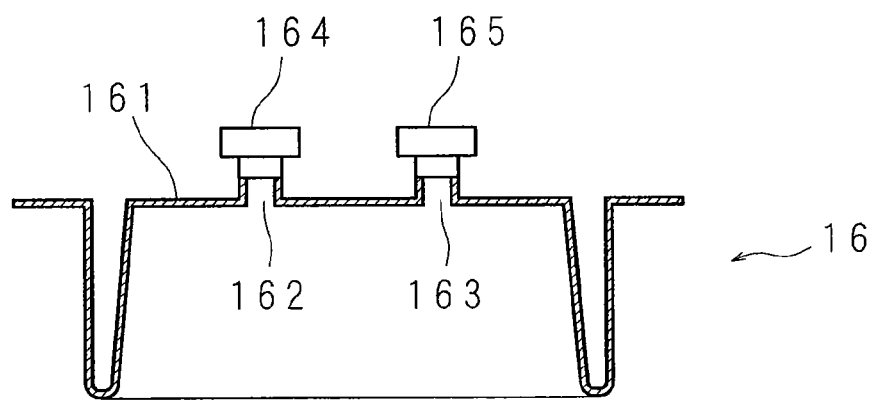

F I G. 2 1
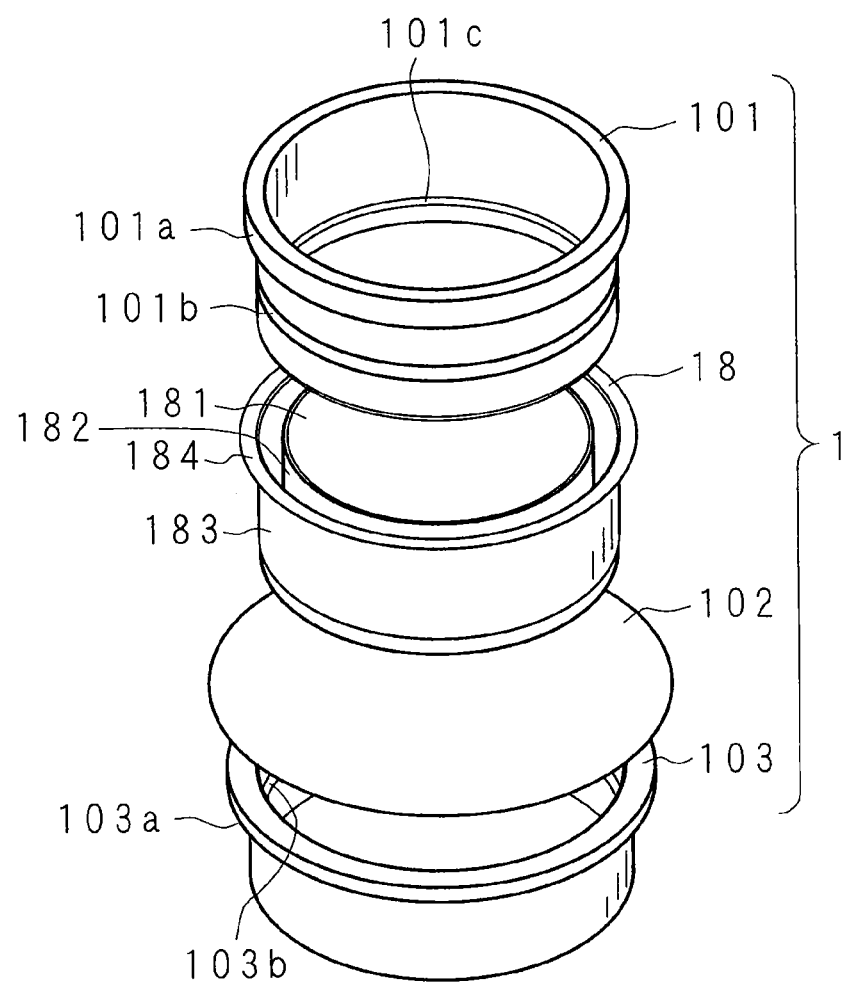

F I G. 3 1
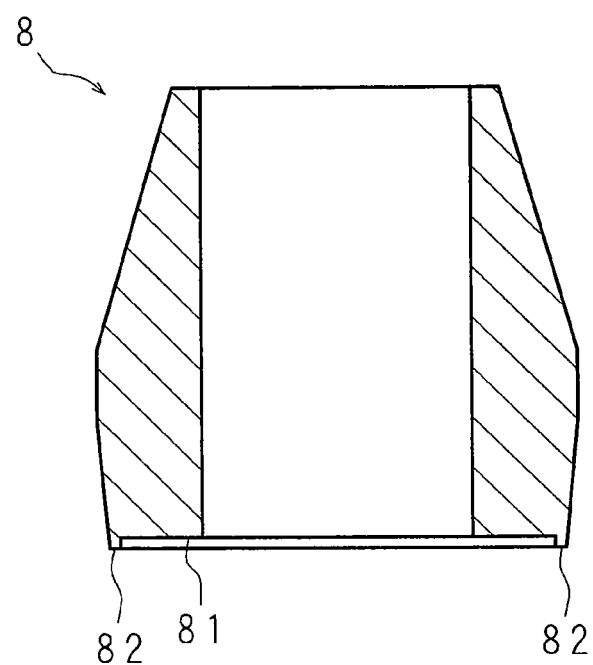

F I G. 3 3
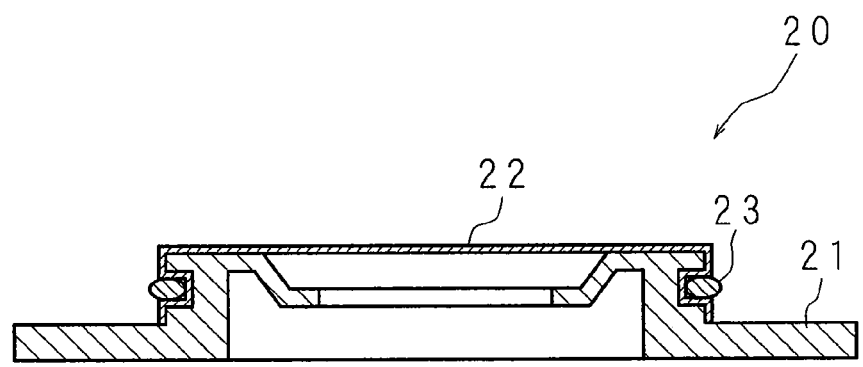

SAMPLE CELL FOR FLUORESCENT X-RAY ANALYSIS AND SAMPLE CELL ASSEMBLY INSTRUMENT

CROSS-REFERENCE TO RELATED APPLICATIONS

This Nonprovisional application claims priority under 35 U.S.C. §119(a) on Patent Application No. 2009-235383 filed in Japan on Oct. 9, 2009 and Patent Application No. 2009-275671 filed in Japan on Dec. 3, 2009, the entire contents of which are hereby incorporated by reference.

BACKGROUND

1. Technical Field

The present invention relates to a sample cell for containing a sample for fluorescent X-ray analysis, and an instrument for assembling the sample cell and, more specifically relates to a sample cell for fluorescent X-ray analysis for containing a volatile sample in a sealed state, and a sample cell assembly instrument for assembling the sample cell for fluorescent X-ray analysis.

2. Description of Related Art

Fluorescent X-ray analysis is an analysis method in which a sample is irradiated with a primary X-ray, a fluorescent X-ray generated from the sample is detected, and qualitative analysis or quantitative analysis of an element contained in the sample is performed on the basis of a spectrum of the fluorescent X-ray. A fluorescent X-ray analyzer for performing the fluorescent X-ray analysis includes an X-ray tube that generates the primary X-ray, an X-ray detector in which a semiconductor detection device or a proportional counter tube is used, and an analyzer that analyzes a wavelength distribution or an energy distribution of an X-ray detected by the X-ray detector. When the fluorescent X-ray analysis is performed, the sample is irradiated with the primary X-ray generated by the X-ray tube, the fluorescent X-ray generated from the sample irradiated with the primary X-ray is detected by the X-ray detector, and the spectrum of the detected fluorescent X-ray is analyzed by the analyzer.

It is possible to utilize such fluorescent X-ray analysis for element analysis of a fluid sample. For example, for the purpose of reducing a hazardous component contained in a liquid fuel such as light oil or the like, the element analysis of the liquid fuel utilizing the fluorescent X-ray analysis is performed. Japanese Patent Application Laid-Open No. 09-127028 describes a fluorescent X-ray analyzer that performs fluorescent X-ray analysis of a fluid sample. When a volatile sample such as the liquid fuel or the like is analyzed, the sample is contained inside a sealed sample cell in order to prevent a reduction or deterioration of the sample resulting from its volatilization. Japanese Patent Application Laid-Open No. 09-127028 describes a technique in which a fluid sample is contained inside a sample cell of which one surface is sealed with an X-ray transmission sheet that allows transmission of the X-ray, the sample inside the sample cell is irradiated with the primary X-ray through the X-ray transmission sheet serving as the bottom surface of the sample cell, and the fluorescent X-ray emitted through the X-ray transmission sheet is detected. In addition, Japanese Patent Application Laid-Open No. 07-134082 describes a sample cell in which a fluid sample is enclosed between two sheets.

Further, Japanese Unexamined Patent Application Laid-Open No. 09-257674 discloses a sample cell that contains a fluid sample. The sample cell includes a sample cup, an X-ray transmission sheet that allows transmission of the X-ray, and an outer frame that externally fits on the sample cup. When the sample cell is assembled, the fluid sample is injected into the sample cup having an upper surface serving as an opening portion, the X-ray transmission sheet is placed on the upper surface of the sample cup, and the outer frame is fitted on the sample cup from the upper side of the sample cup such that the outer frame is externally fitted on the sample cup with the X-ray transmission sheet interposed therebetween. The X-ray transmission sheet is pulled from its center in a radial direction when the outer frame is fitted, and a circumferential portion thereof is interposed between the outer circumference of the sample cup and the outer frame, whereby the X-ray transmission sheet is disposed in tension so as to seal the opening portion of the sample cup. When the fluorescent X-ray analysis is performed, the X-ray transmission sheet is used as the bottom surface of the sample cell, the sample inside the sample cell is irradiated with the primary X-ray through the X-ray transmission sheet, and the fluorescent X-ray emitted through the X-ray transmission sheet is detected.

SUMMARY

When trying to fully fill the sample cell with the fluid sample, the fluid sample overflows from the sample cell so that it is not possible to fully fill the sample cell. As a result, the fluid sample and a small amount of air are enclosed inside the sample cell. When the fluid sample is a liquid having high volatility such as fuel or the like, the fluid sample is volatilized inside the sample cell with the passage of time to increase an internal pressure of the sample cell. When the internal pressure of the sample cell is increased, a sheet sealing the sample cell is expanded. When the sheet through which the fluorescent X-ray from the sample is transmitted is expanded, the problem occurs that a distance between the sample and a detector detecting the fluorescent X-ray is fluctuated, the intensity of the fluorescent X-ray detected by the detector is fluctuated, and it is not possible to perform high-precision element analysis accordingly.

In addition, conventionally, when the sample cell is assembled, since the X-ray transmission sheet is placed on the opening portion of the sample cup after the fluid sample is injected thereinto and, then the outer frame is fitted thereon, there are cases where the fluid sample adheres to the X-ray transmission sheet before the assembly of the sample cell is completed. The portion of the X-ray transmission sheet to which the fluid sample has adhered becomes less slidable when the portion comes in contact with the rim of the sample cup, which results in the occurrence of a cockle when the X-ray transmission sheet is disposed in tension. Since the X-ray transmission sheet serves as the bottom surface of the sample cell when the fluorescent X-ray analysis is performed, in the case where the cockle has occurred, the fluid sample may leak, and the problem is encountered that the distance between the sample and the detector is fluctuated so that it is not possible to perform high-precision element analysis. Moreover, when the outer frame is fitted, tension pulling the X-ray transmission sheet in a radial direction is apt to be nonuniform, and the nonuniform tension results in the occurrence of the cockle in the X-ray transmission sheet.

The present invention has been achieved in view of the foregoing circumstances, and an object thereof is to provide a sample cell for fluorescent X-ray analysis allowing high-precision element analysis by preventing expansion of a sheet through which a fluorescent X-ray is transmitted even when an internal pressure is increased.

Another object of the present invention is to provide a sample cell assembly instrument that assembles a sample cell so as to be able to prevent expansion of an X-ray transmission sheet during fluorescent X-ray analysis by assembling the sample cell such that a portion other than the X-ray transmission sheet is deformable so as to be able to accommodate an increase in an internal pressure of the sample cell.

Still another object of the present invention is to provide a sample cell assembly instrument capable of preventing the occurrence of a cockle in an X-ray transmission sheet when a sample cell is assembled.

A sample cell for fluorescent X-ray analysis according to the present invention is a sample cell for fluorescent X-ray analysis having a window part for emitting a fluorescent X-ray from a sample contained therein to an outside, and used in a sealed state with the sample contained therein in which a deforming part deformable so as to increase an internal capacity before the window part is deformed when an internal pressure is increased in the sealed state is provided.

In the present invention, the sample cell for fluorescent X-ray analysis having the window part for emitting the fluorescent X-ray from the sample, and used in the sealed state has the deforming part that is deformed so as to increase the internal capacity in response to the increase in pressure before the window part sealed with the X-ray transmission sheet or the like is deformed. When the internal pressure of the sample cell for fluorescent X-ray analysis that is sealed with the sample contained therein is increased, the deforming part is deformed to increase the internal capacity, and the increase in pressure is thereby relieved.

In the sample cell for fluorescent X-ray analysis according to the present invention, as the deforming part, a part of a wall other than the window part is formed of a sheet folded so as to be able to be unfolded outwardly.

In the present invention, since the wall other than the window part is formed of the sheet folded so as to be able to be unfolded outwardly, when the internal pressure is increased, the folded sheet is unfolded, and the internal capacity is thereby increased before the window part is deformed.

In the sample cell for fluorescent X-ray analysis according to the present invention, as the deforming part, a part of a wall other than the window part is formed of a sheet that is expanded in response to an increase in pressure.

In the present invention, since the wall other than the window part is formed of the expandable sheet, when the internal pressure is increased, the sheet is expanded outwardly in response to the increase in pressure, and the internal capacity is thereby increased before the window part is deformed.

In the sample cell for fluorescent X-ray analysis according to the present invention, as the deforming part, a portion other than the window part is provided with a bellows deformable in a direction that allows an increase in the internal capacity.

In the present invention, since the portion other than the window part is provided with the bellows deformable in the direction that allows the increase in the internal capacity, when the internal pressure is increased, the bellows is deformed in response to the increase in pressure, and the internal capacity is thereby increased before the window part is deformed.

In the sample cell for fluorescent X-ray analysis according to the present invention, as the deforming part, a part of a wall other than the window part is formed of a deformable sheet, and the wall is convexly deformed inwardly in advance.

In the present invention, since the wall other than the window part is formed of the deformable sheet, and the wall is convexly deformed inwardly in advance, when the internal pressure is increased, the sheet is outwardly deformed in response to the increase in pressure, and the internal capacity is thereby increased before the window part is deformed.

In the sample cell for fluorescent X-ray analysis of the present invention, even when the sample is volatilized to increase the internal pressure of the sample cell for fluorescent X-ray analysis during the execution of the fluorescent X-ray analysis, the deforming part is deformed to relieve the increase in pressure, and hence the window part in the sealed state is not deformed. Since the window part is not deformed, a distance between the sample and a detector detecting the fluorescent X-ray is not fluctuated, and the intensity of the detected fluorescent X-ray is not fluctuated as well. Consequently, the intensity of the fluorescent X-ray is not changed by factors other than an element distribution in the sample, and hence it becomes possible to perform the element analysis of the sample by the fluorescent X-ray analysis with high precision.

A sample cell assembly instrument according to the present invention is a sample cell assembly instrument used when a sample cell for fluorescent X-ray analysis is assembled by containing a sample in a sample cup, sealing an opening portion of the sample cup in which the sample is contained with an X-ray transmission sheet, and fitting an outer frame on the sample cup with the X-ray transmission sheet interposed therebetween, including a sample cup placing stand that is a stand for placing the sample cup thereon, and has a positioning part positioning the sample cup when the sample cup with the opening portion disposed on an upper side is placed, and a pushing-up part pushing up an, end surface disposed on a lower side of the sample cup to convexly deform the end surface inwardly of the sample cup when the outer frame is fitted on the placed sample cup from above.

In the sample cell assembly instrument according to the present invention, a cylindrical inner frame is fitted in the sample cup on a side of the end surface thereof and an end portion of the inner frame projects above the end surface, the positioning part is a column raised on a flat surface, an outer diameter of the column is a size that allows the column to be fitted in the inner frame, a height of the column is smaller than a distance from the end portion of the inner frame to the end surface of the sample cup, and the pushing-up part is a projection projecting in a center of an upper surface of the column.

In the present invention, when the operation of sealing the opening portion of the sample cup with the X-ray transmission sheet with the opening portion disposed on the upper side is performed, by placing the sample cup on the sample cup placing stand having the projection, the end surface of the sample cup is convexly deformed inwardly.

The sample cell assembly instrument according to the present invention further includes a sheet placing instrument that is separate from the sample cup placing stand, has a tubular shape, has both end surfaces in parallel with each other and orthogonal to an axis, has an inner diameter larger than an outer diameter of the sample cell, has a height when placed on the sample cup placing stand higher than the sample cup, is placed on the sample cup placing stand so as to surround the sample cup, and is used in order to place the X-ray transmission sheet thereon.

In the present invention, when the X-ray transmission sheet is disposed on the sample cup containing the sample, the X-ray transmission sheet is placed on the sheet placing instrument that surrounds the sample cup on the sample cup placing stand and, in addition, is higher than the sample cup, whereby it is possible to dispose the X-ray transmission sheet on the sample cup without contact with the sample.

The sample cell assembly instrument according to the present invention further includes an outer frame fitting instrument that is separate from the sample cup placing stand and the sheet placing instrument, has a tubular shape, has an inner diameter allowing the outer frame to be fitted therein, has an outer diameter smaller than the inner diameter of the sheet placing instrument, has a height higher than the outer frame, and is used in order to push the outer frame fitted therein toward the sample cup from an upper side of the X-ray transmission sheet placed on the sheet placing instrument to fit the outer frame on the sample cup.

In the present invention, when the outer frame is fitted on the sample cup in order to fix the X-ray transmission sheet, since the outer frame is inserted from the upper side of the X-ray transmission sheet placed on the sheet placing instrument to be fitted by using the tubular outer frame fitting instrument that is externally fitted on the outer frame, the outer frame fitting instrument is guided by the inner wall of the sheet placing instrument to insert the outer frame substantially vertically, and the X-ray transmission sheet is uniformly spread.

In the sample cell assembled by using the sample cell assembly instrument of the present invention, even when the fluid sample is volatilized inside the sample cell to increase the internal pressure, the end surface of the sample cup that has been convexly deformed inwardly in advance is outwardly deformed, and the X-ray transmission sheet through which the primary X-ray and the fluorescent X-ray are transmitted is not expanded. Consequently, the intensity of the fluorescent X-ray is not changed by factors other than the element distribution in the fluid sample, and hence it becomes possible to perform the element analysis of the fluid sample by the fluorescent X-ray analysis with high precision.

The above and further objects and features of the invention will more fully be apparent from the following detailed description with accompanying drawings.

BRIEF DESCRIPTION OF THE SEVERAL VIEWS OF THE DRAWINGS

FIG. 1 is a schematic view illustrating a structure of a fluorescent X-ray analyzer according to Embodiment 1;

FIGS. 10A to 10D are schematic cross-sectional views illustrating usage of the sample cell according to the third example of Embodiment 1;

FIGS. 13A and 13B are schematic cross-sectional views of a sample cup according to a fifth example of Embodiment 1;

FIGS. 15A and 15B are schematic cross-sectional views of a sample cup according to a sixth example of Embodiment 1;

FIG. 21 is an exploded perspective view illustrating the structure of the sample cell;

FIG. 31 is a cross-sectional view of the cell holder assembly instrument taken along its axis;

FIG. 33 is a cross-sectional view illustrating the assembled cell holder;

DETAILED DESCRIPTION

Figure 2:
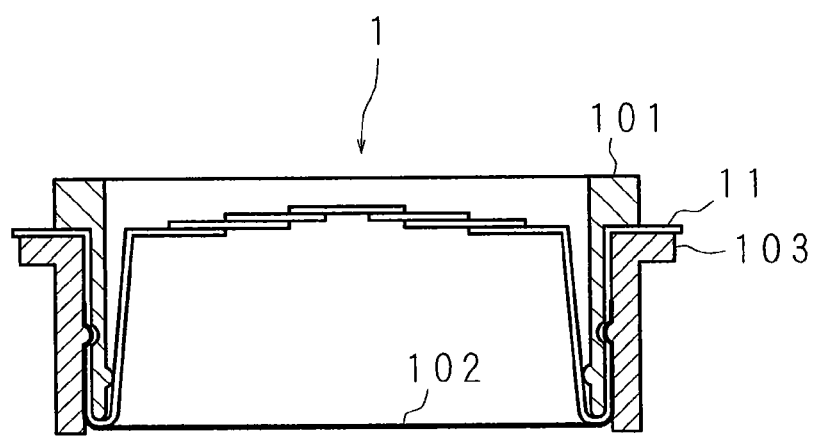
FIG. 2 is a cross-sectional view illustrating a structure of a sample cell.

The present invention will be specifically described hereinbelow with reference to the accompanying drawings illustrating embodiments thereof.

(First Example of Embodiment 1)

FIG. 1 is a schematic view illustrating a structure of a fluorescent X-ray analyzer according to Embodiment 1. The fluorescent X-ray analyzer includes a housing 5 that is formed into a box-like shape with a material blocking an X-ray, and an upper portion of the housing 5 is formed into a flat surface. An opening portion is formed in the center of the flat surface of the upper portion of the housing 5, and a cell holder 2 is attached to be fitted in the opening portion. A sample cell (sample cell for fluorescent X-ray analysis) 1 in which a sample to be analyzed is contained is placed on the cell holder 2. In the fluorescent X-ray analyzer, there is provided a cover 6 that covers at least a part of the upper surface of the housing 5 including the opening portion, and the cell holder 2 and the sample cell 1 placed on the cell holder 2 are covered with the cover 6. The sample cell 1 is a cell for containing a fluid sample such as a powder, a liquid fuel, or the like, and is formed into a cup-like shape. The cell holder 2 is provided with an X-ray transmission sheet 22 that allows transmission of the X-ray, and a lower surface of the sample cell 1 is constituted by an X-ray transmission sheet 102.

A hollow measurement chamber 51 is formed inside the housing 5, and the housing 5 includes an X-ray tube 3 that emits primary X-rays into the measurement chamber 51 and an X-ray detector 4. The X-ray tube 3 is disposed at a position where the primary X-rays are emitted toward the opening portion of the housing 5. When fluorescent X-ray analysis is performed, since the cell holder 2 and the sample cell 1 are disposed at the position of the opening portion of the housing 5, the primary X-rays generated from the X-ray tube 3 are transmitted through the X-ray transmission sheet 22 of the cell holder 2 and the X-ray transmission sheet 102 of the sample cell 1, and the sample inside the sample cell 1 is irradiated with the primary X-rays. The sample inside the sample cell 1 that is irradiated with the primary X-rays generates fluorescent X-rays, and the fluorescent X-rays are transmitted through the X-ray transmission sheet 102 and the X-ray transmission sheet 22 of the cell holder 2 to be emitted into the measurement chamber 51. The X-ray detector 4 is disposed at a position where the fluorescent X-rays generated from the sample inside the sample cell 1 can be detected. Paths along which the primary X-rays emitted by the X-ray tube 3 and the fluorescent X-rays detected by the X-ray detector 4 travel are indicated by broken-line arrows in FIG. 1.

At an emission port of the X-ray tube 3 from which the primary X-rays are emitted, there is provided an openable and closable shutter that is not shown. The X-ray tube 3 constantly generates the X-rays in order to stabilize an output of the primary X-rays, and emits the primary X-rays by opening the shutter. The X-ray detector 4 uses a proportional counter tube as a detection device, and outputs electric signals in proportion to energy of the fluorescent X-rays entering the proportional counter tube. It is to be noted that the X-ray detector 4 may use a detection device other than the proportional counter tube, such as a semiconductor detection device or the like. The X-ray detector 4 is connected to a signal analysis unit (not shown) that is constituted by using a personal computer or the like. The signal analysis unit performs processing for receiving the electric signals outputted by the X-ray detector 4, counting the intensities and the number of the respective electric signals in correspondence to the energy of the fluorescent X-rays, and obtaining the relationship between the energy of the fluorescent X-rays and the counted number, namely, the spectrum of the fluorescent X-rays. It is to be noted that the signal analysis unit may further perform qualitative analysis or quantitative analysis of an element having generated the fluorescent X-rays on the basis of the obtained spectrum of the fluorescent X-rays.

When the cell holder 2 is attached to the opening portion of the housing 5, the measurement chamber 51 in the housing 5 is a space sealed by the cell holder 2. In the housing 5, there is formed a supply port 52 that communicates with the measurement chamber 51 and supplies a gas into the measurement chamber 51. A gas supply pipe (not shown) for supplying the gas is coupled to the supply port 52. When the fluorescent X-ray analysis is performed, a gas such as a helium gas or a nitrogen gas is supplied into the measurement chamber 51 from the supply port 52, and the air in the measurement chamber 51 is replaced with the gas. In FIG. 1, the supplied gas is indicated by solid-line arrows. The X-ray tube 3 is attached to the housing 5 via a sealing metal foil 31 so as not to come in direct contact with the gas replaced with the air in the measurement chamber 51. Depending upon the type of the sample to be analyzed, there are cases where a primary filter is used in order to reduce the background of each spectrum of the fluorescent X-rays, and the primary X-rays are emitted from the X-ray tube 3 through the primary filter. In such cases, the primary filter may be used instead of the sealing metal foil 31.

When the sample cell 1 is placed on the cell holder 2, a space is formed between the X-ray transmission sheet 22 of the cell holder 2 and the X-ray transmission sheet 102 of the sample cell 1. The fluorescent X-ray analyzer has a supply mechanism (not shown) for supplying the gas into the space between the X-ray transmission sheets 22 and 102. With the function of the supply mechanism, the air in the space between the X-ray transmission sheets 22 and 102 is also replaced with the gas such as the helium gas or the nitrogen gas.

Figure 3:
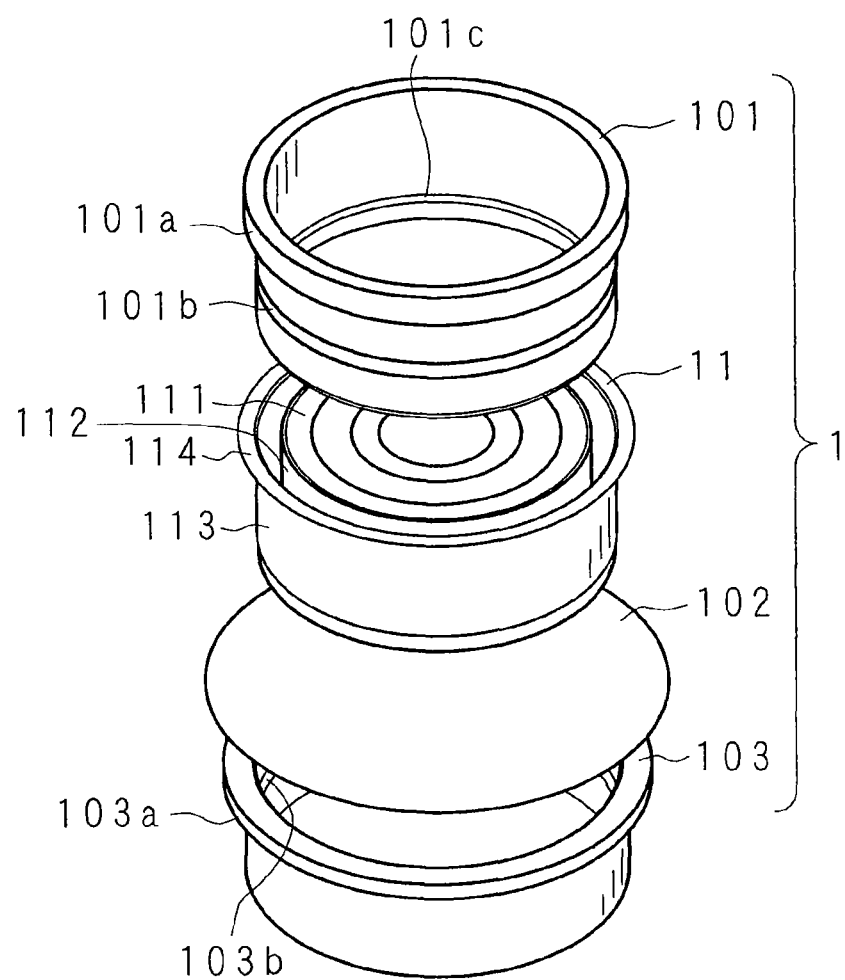
FIG. 3 is an exploded perspective view illustrating the structure of the sample cell.

FIG. 2 is a cross-sectional view illustrating the structure of the sample cell 1, while FIG. 3 is an exploded perspective view illustrating the structure of the sample cell 1. The sample cell 1 includes a cell inner frame 101, a sample cup 11, a cell outer frame 103, and the X-ray transmission sheet 102. The cell inner frame 101 is in a cylindrical shape, and is formed of a plastic such as polyethylene or the like, or a metal. A flange part 101*a* is provided completely around an outer circumferential surface in an upper end portion of the cell inner frame 101. In addition, a groove 101*b* is formed completely around the outer circumferential surface at the center in an axial direction of the cell inner frame 101, and an annular projection part 101*c* is provided completely around an inner circumferential surface of the cell inner frame 101.

The sample cup 11 is formed by bending a sheet such as a flexible plastic film or the like. The sample cup 11 has a cylindrical sample containing part 112 having a cup end surface 111 on one end and an opening portion on the other end, a cylindrical surrounding part 113 that is coupled to the opening portion of the sample containing part 112 and provided at a predetermined distance from an outer circumferential surface of the sample containing part 112 so as to surround the outer circumferential surface of the sample containing part 112, and a flange part 114 provided completely around an outer circumferential surface in an end portion of the surrounding part 113. In addition, as will be described later, the cup end surface 111 is formed flat by folding a sheet.

The outer diameter of the sample containing part 112 is smaller than the inner diameter of the cell inner frame 101, and the inner diameter of the surrounding part 113 is substantially equal to the outer diameter of the cell inner frame 101. In addition, the height of the cell inner frame 101 without the flange part 101*a* (a vertical length) is slightly lower than the height of a space between the sample containing part 112 and the surrounding part 113. Consequently, it is possible to insert the cell inner frame 101 from above into the space between the sample containing part 112 and the surrounding part 113 until the flange part 101a of the cell inner frame 101 comes in contact with the flange part 114 of the sample cup 11. When the cell inner frame 101 is inserted into the sample cup 11 in this manner, the cell inner frame 101 is fitted in the surrounding part 113 of the sample cup 11, and a gap is formed between the inner circumferential surface of the cell inner frame 101 and the outer circumferential surface of the sample containing part 112 of the sample cup 11.

The X-ray transmission sheet 102 is a substantially circular thin sheet having a diameter sufficiently larger than the outer diameter of the sample cup 11, and is formed of a material that does not allow the passage of a fluid sample such as a liquid fuel or the like but allows transmission of the X-rays. The X-ray transmission sheet 102 is made of, e.g., a polyester sheet. The X-ray transmission sheet 102 seals the sample cup 11 by covering the opening portion of the sample cup 11 containing the sample, and serves as a bottom surface of the sample cup 11 (i.e., a bottom surface of the sample cell 1).

The cell outer frame 103 is in a cylindrical shape, and is formed of a plastic such as polyethylene or the like, or a metal. The inner diameter of the cell outer frame 103 is slightly larger than the outer diameter of the sample cup 11, and the sample cup 11 with the cell inner frame 101 inserted into the space between the sample containing part 112 and the surrounding part 113 may be inserted from a side of the opening portion to be fitted in the cell outer frame 103. At this point, the sample cup 11 with its opening portion covered with the X-ray transmission sheet 102 is fitted in the cell outer frame 103, and an outer edge portion of the X-ray transmission sheet 102 is thereby interposed between the outer circumferential surface of the sample cup 11 and the inner circumferential surface of the cell outer frame 103. Consequently, the X-ray transmission sheet 102 is firmly fixed as the bottom surface of the sample cell 1 such that the fluid sample inside the sample cup 11 is not leaked from the opening portion.

A flange part 103a is provided completely around an outer circumferential surface in an upper end portion of the cell outer frame 103, and the flange 103a supports the cell inner frame 101 and the sample cup 11 that are fitted in the cell outer frame 103 at their respective flange portions 101a and 114. In addition, a projection part 103b is provided completely around the inner circumferential surface of the cell outer frame 103 in a position in correspondence to the groove 101b provided in the outer circumferential surface of the cell inner frame 101, and the projection part 103b is engaged with the groove 101b of the cell inner frame 101 fitted in the cell outer frame 103 with the surrounding part 113 of the sample cup 11 and the X-ray transmission sheet 102 interposed therebetween. With this structure, the sample cup 11 and the X-ray transmission sheet 102 are firmly held between the cell inner frame 101 and the cell outer frame 103.

The cell holder 2 is made of a metal such as copper, aluminum, or the like, and is formed into an annular shape having an opening portion formed in the center. The X-ray transmission sheet 22 is disposed on the opening portion of the cell holder 2 so as to close the opening portion. The cell holder 2 having the X-ray transmission sheet 22 is attached to be fitted in the opening portion of the housing 5, and the opening portion of the housing 5 is thereby closed. The sample cell 1 is placed on the cell holder 2 such that the X-ray transmission sheet 102 of the sample cell 1 and the X-ray transmission sheet 22 of the cell holder 2 oppose each other. The primary X-rays from the X-ray tube 3 are transmitted through the X-ray transmission sheet 22 of the cell holder 2 and the X-ray transmission sheet 102 of the sample cell 1 to be emitted to the sample inside the sample cell 1. Consequently, the X-ray transmission sheet 102 of the sample cell 1 functions as a sealed window part in the present invention.

Figure 4A:
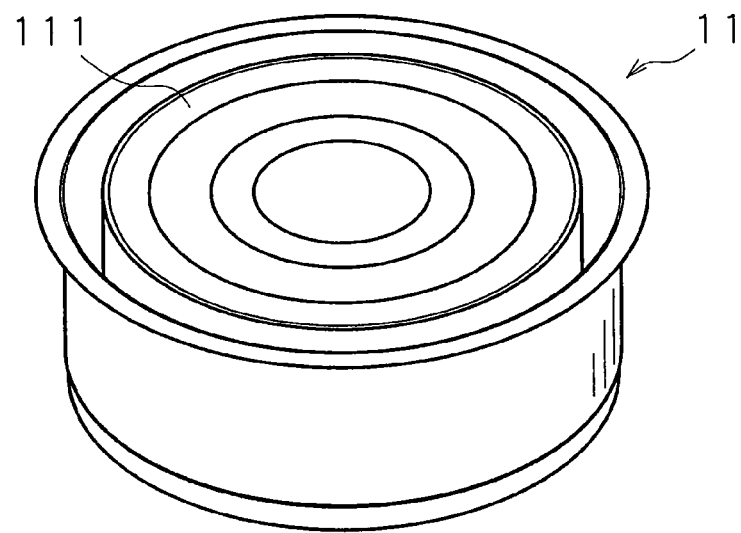
FIGS. 4A and 4B are schematic perspective views of a sample cup according to a first example of Embodiment 1.
Figure 4B:
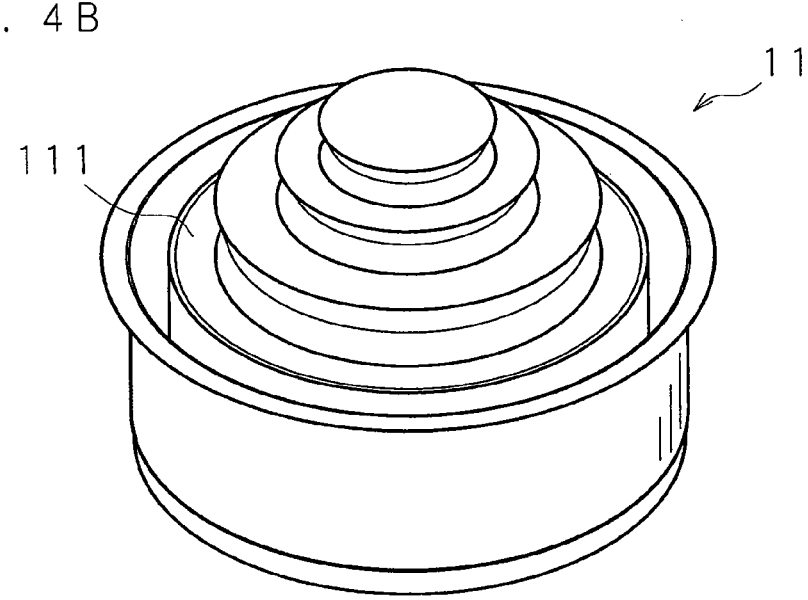

FIGS. 4A and 4B are schematic perspective views of the sample cup 11 according to a first example of Embodiment 1. The cup end surface 111 of the sample cup 11 is formed flat by folding a sheet larger than the area of the cup end surface 111. FIG. 4A illustrates a state where the sheet is folded, while FIG. 4B illustrates a state where the sheet is unfolded. The cup end surface 111 is formed by concentrically folding the sheet in a shape that increases in height toward the center. In addition, in the cup end surface 111, the sheet is folded such that the sheet is unfolded when a pressure from the inside of the sample cup 11 is increased. Since the cup end surface 111 is formed in this manner, when the pressure from the inside of the sample cup 11 is normal, the cup end surface 111 is flat, as illustrated in FIG. 4A. On the other hand, when the pressure from the inside of the sample cup 11 is increased, as illustrated in FIG. 4B, the sheet constituting the cup end surface 111 is unfolded, and the cup end surface 111 is deformed into a shape that is expanded outwardly of the sample cup 11. The cup end surface 111 is deformed into the shape that is expanded outwardly of the sample cup 11, and the internal capacity of the sample cup 11, i.e., the internal capacity of the sample cell 1 containing the sample is thereby increased. The cup end surface 111 functions as a deforming part in the present invention. It is to be noted that the cup end surface 111 may be formed by folding a sheet in a different shape as long as the sheet is unfolded to be expanded outwardly of the sample cup 11 when the pressure from the inside of the sample cup 11 is increased.

Figure 5A:
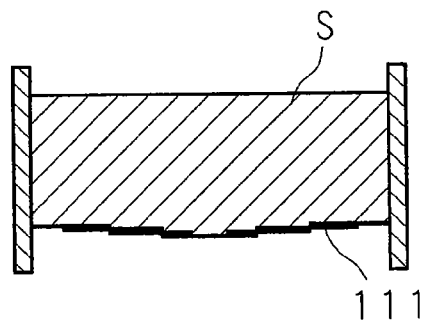
FIGS. 5A to 5D are schematic cross-sectional views illustrating usage of a sample cell according to the first example of Embodiment 1.
Figure 5B:
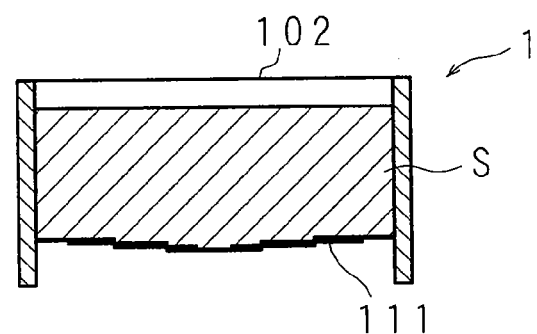

FIGS. 5A to 5D are schematic cross-sectional views illustrating usage of the sample cell 1 according to the first example of Embodiment 1. First, as illustrated in FIG. 5A, the sample cup 11 is put from above on the cell inner frame 101 with the flange part 101a disposed on the lower side, and a fluid sample S is injected from the opening portion of the sample cup 11 into the sample cup 11 with the cup end surface 111 disposed on the lower side. Next, the opening portion of the sample cup 11 is covered with the X-ray transmission sheet 102, and the cell outer frame 103 is externally fitted thereon from above. In this manner, the sample cell 1 is assembled, and the fluid sample S is contained. As illustrated in FIG. 5B, in the state where the sample cell 1 is assembled, the sample cell 1 is sealed with the X-ray transmission sheet 102, and the fluid sample S and a small amount of air are enclosed inside the sample cell 1.

Figure 5C:
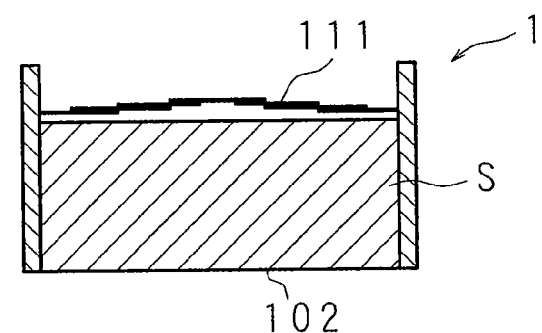
Figure 5D:
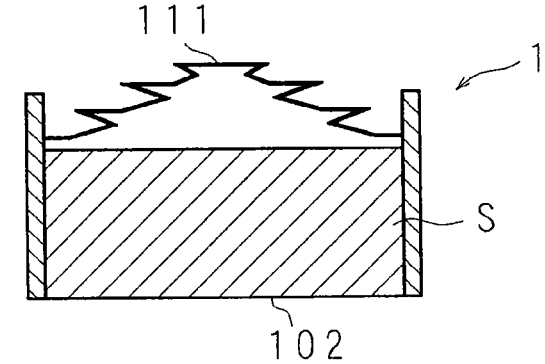

Subsequently, the sample cell 1 is turned upside down, and placed on the cell holder 2 with the X-ray transmission sheet 102 serving as the bottom surface and the cup end surface 111 disposed on the upper side, as illustrated in FIG. 5C. With the sample cell 1 placed on the cell holder 2, the primary X-rays are emitted from the X-ray tube 3, and the fluorescent X-ray analysis is thereby performed. The primary X-rays from the X-ray tube 3 are emitted from the lower side in the drawing illustrated in FIG. 5C, the primary X-rays are transmitted through the X-ray transmission sheet 102 to be emitted to the fluid sample S inside the sample cell 1, and the fluorescent X-rays generated from the fluid sample S are transmitted through the X-ray transmission sheet 102 to be emitted. When the fluid sample S is volatilized with the passage of time to increase the internal pressure of the sample cell 1 during the execution of the fluorescent X-ray analysis, the folded sheet constituting the cup end surface 111 is unfolded in response to the increase in pressure. As illustrated in FIG. 5D, the cup end surface 111 is deformed so as to be expanded outwardly of the sample cell 1, and the internal capacity of the sample cell 1 is thereby increased. The internal capacity of the sample cell 1 is increased to relieve the increase in the internal pressure of the sample cell 1, and hence the expansion of the X-ray transmission sheet 102 due to the increase in pressure is prevented.

As has been described above, in the fluorescent X-ray analyzer using the sample cell 1 according to the first example, even when the fluid sample S is volatilized inside the sample cell 1 to increase the internal pressure of the sample cell 1, the X-ray transmission sheet 102 as the window part through which the primary X-rays and the fluorescent X-rays are transmitted is not expanded. Since the X-ray transmission sheet 102 allowing the transmission of the fluorescent X-rays is not expanded, a distance between the fluid sample S and the X-ray detector 4 detecting the fluorescent X-rays is not fluctuated, and the intensities of the fluorescent X-rays detected by the X-ray detector 4 are not fluctuated as well. Consequently, the intensities of the fluorescent X-rays are not changed by factors other than an element distribution in the fluid sample S, and hence it becomes possible to perform the element analysis of the fluid sample S by the fluorescent X-ray analysis with high precision.

(Second Example of Embodiment 1)

Figure 6A:
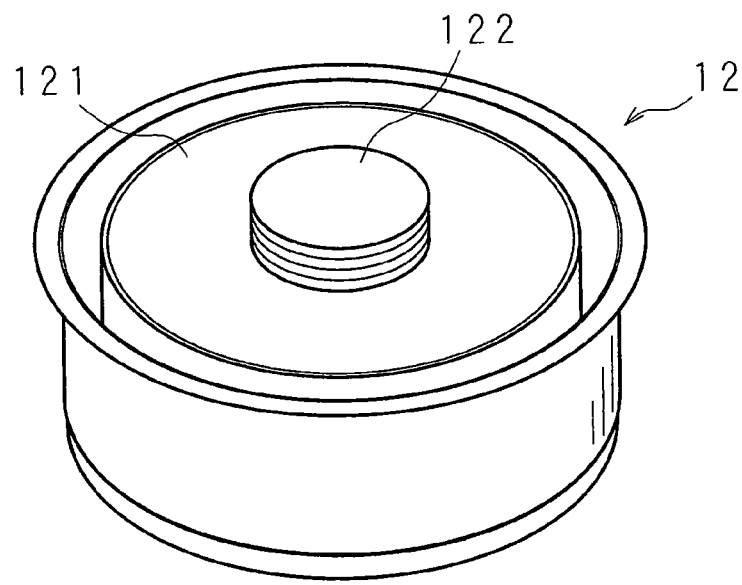
FIGS. 6A and 6B are schematic perspective views of a sample cup according to a second example of Embodiment 1.
Figure 6B:
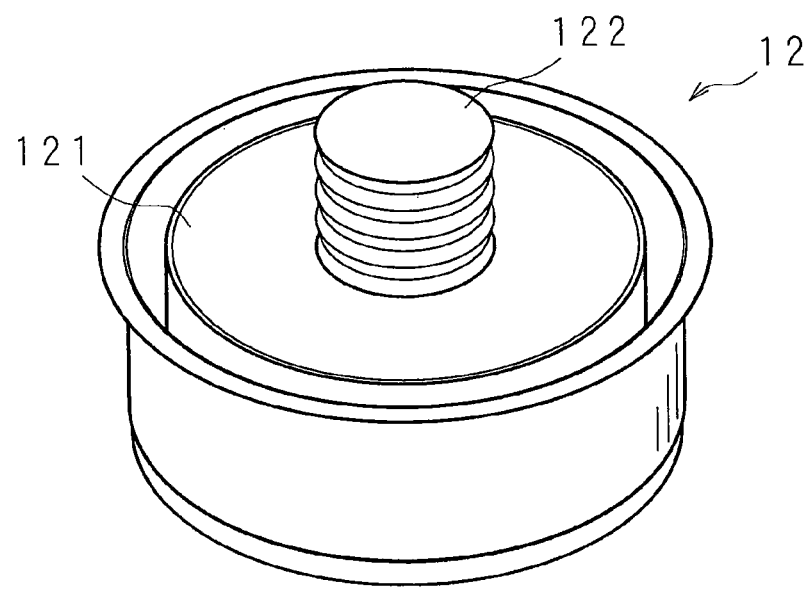

In a second example of Embodiment 1, the structure of the fluorescent X-ray analyzer is the same as that in the first example, but the shape of the sample cup of the sample cell 1 is different. FIGS. 6A and 6B are schematic perspective views of a sample cup 12 according to the second example of Embodiment 1. On a cup end surface 121 of the sample cup 12, there is provided a bellows 122 that is hollow and extendable. FIG. 6A illustrates a state where the bellows 122 is contracted, while FIG. 6B illustrates a state where the bellows 122 is extended. As illustrated in FIG. 6B, when the bellows 122 is extended, the bellows 122 is formed to be extended outwardly of the sample cup 12. The hollow inside the bellows 122 is coupled to the space inside the sample cell 1 formed by the sample cup 12. As a result, when the pressure from the inside of the sample cup 12 is increased, as illustrated in FIG. 6B, the bellows 122 is extended outwardly of the sample cup 12, and the hollow inside the bellows 122 coupled to the space inside the sample cell 1 is expanded. Since the bellows 122 is provided on the cup end surface 121 in this manner, when the pressure from the inside of the sample cup 12 is normal, the bellows 122 is contracted as illustrated in FIG. 6A and, when the pressure from the inside of the sample cup 12 is increased, the bellows 122 is deformed into a shape that is extended outwardly of the sample cup 12, as illustrated in FIG. 6B. The bellows 122 is deformed into the shape that is extended outwardly of the sample cup 12, and the internal capacity of the sample cup 12 including the hollow inside the bellows 122, i.e., the internal capacity of the sample cell 1 for containing the sample is thereby increased. The bellows 122 functions as the deforming part in the present invention. The structure of the sample cell 1 other than the sample cup 12 is the same as that in the first example.

Figure 7A:
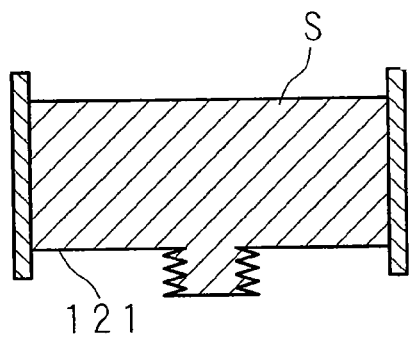
FIGS. 7A to 7D are schematic cross-sectional views illustrating usage of a sample cell according to the second example of Embodiment 1.
Figure 7B:
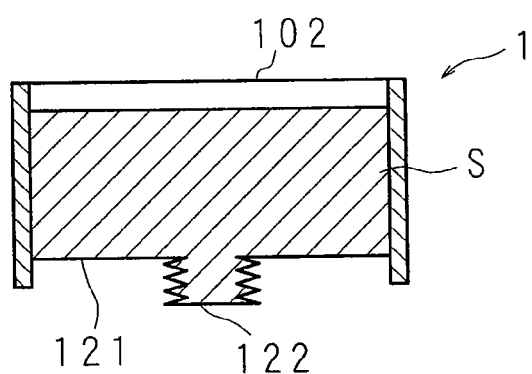
Figure 7C:
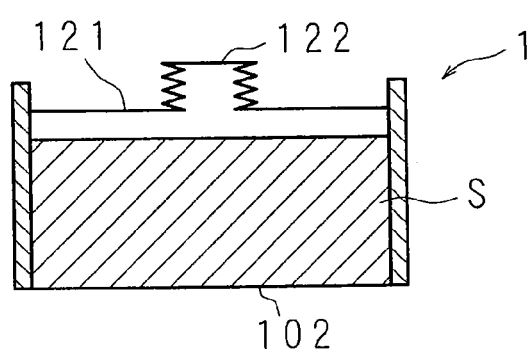

FIGS. 7A to 7D are schematic cross-sectional views illustrating usage of the sample cell 1 according to the second example of Embodiment 1. First, as illustrated in FIG. 7A, the sample cup 12 is put on the cell inner frame 101 from above, and the fluid sample S is injected from the opening portion of the sample cup 12 into the sample cup 12 with the cup end surface 121 disposed on the lower side. Next, as illustrated in FIG. 7B, the opening portion of the sample cup 12 is covered with the X-ray transmission sheet 102, and the cell outer frame 103 is externally fitted thereon. In this manner, the sample cell 1 is assembled, and the fluid sample S is contained. Subsequently, the sample cell 1 is turned upside down and, as illustrated in FIG. 7C, the sample cell 1 is placed on the cell holder 2 with the X-ray transmission sheet 102 serving as the bottom surface and the cup end surface 121 disposed on the upper side, and the fluorescent X-ray analysis is performed. In this state, the bellows 122 is contracted.

Figure 7D:
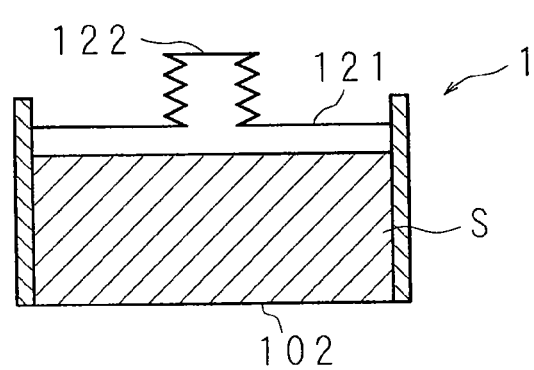

When the fluid sample S is volatilized with the passage of time to increase the internal pressure of the sample cell 1 during the execution of the fluorescent X-ray analysis, the bellows 122 is extended in response to the increase in pressure. As illustrated in FIG. 7D, the bellows 122 is deformed while being extended outwardly of the sample cell 1, and the internal capacity of the sample cell 1 is thereby increased. Since the internal capacity of the sample cell 1 is increased to relieve the increase in the internal pressure of the sample cell 1, the expansion of the X-ray transmission sheet 102 due to the increase in pressure is prevented.

As has been described above, in the fluorescent X-ray analyzer using the sample cell 1 according to the second example as well, when the fluid sample S is volatilized inside the sample sell 1 to increase the internal pressure of the sample cell 1, the X-ray transmission sheet 102 as the window part through which the primary X-rays and the fluorescent X-rays are transmitted is not expanded. Consequently, the distance between the fluid sample S and the X-ray detector 4 detecting the fluorescent X-rays is not fluctuated, and the intensities of the fluorescent X-rays detected by the X-ray detector 4 are not fluctuated, and hence it becomes possible to perform the element analysis of the fluid sample S by the fluorescent X-ray analysis with high precision.

Figure 8A:
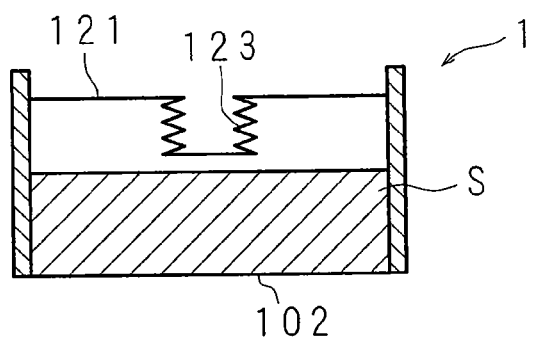
FIGS. 8A and 8B are schematic cross-sectional views illustrating a configuration in which a bellows is provided on the inside of a cup end surface.
Figure 8B:
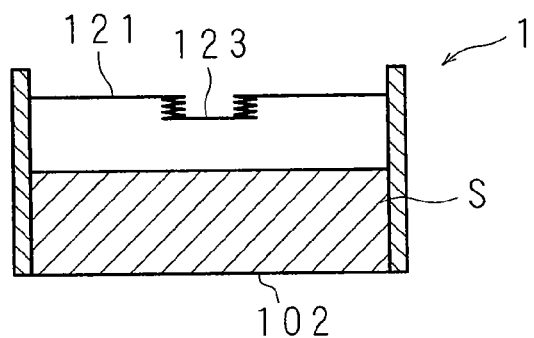

Although in each of FIGS. 6A and 6B, and FIGS. 7A to 7D, the bellows 122 is provided on the outside of the cup end surface 121, the bellows may also be provided on the inside of the cup end surface 121. FIGS. 8A and 8B are schematic cross-sectional views illustrating a configuration in which a bellows 123 is provided on the inside of the cup end surface 121. As illustrated in FIG. 8A, on the cup end surface 121, there is provided the bellows 123 extendable inwardly of the sample cup 12. In the state where the sample cell 1 is assembled and the fluid sample S is contained, and the X-ray transmission sheet 102 is used as the bottom surface and the cup end surface 121 is disposed on the upper side as illustrated in FIG. 8A, the bellows 123 is extended inwardly of the sample cell 1 by gravitation. The sample cell 1 in this state is placed on the cell holder 2, and the fluorescent X-ray analysis is performed. When the fluid sample S is volatilized with the passage of time to increase the internal pressure of the sample cell 1, the bellows 123 is contracted in response to the increase in pressure, as illustrated in FIG. 8B. The bellows 123 is deformed so as to increase the capacity of the sample cell 1 by its contraction. The internal capacity of the sample cell 1 is increased to relieve the increase in the internal pressure of the sample cell 1, and hence the expansion of the X-ray transmission sheet 102 due to the increase in pressure is prevented. Consequently, in this configuration as well, it becomes possible to perform the element analysis of the fluid sample S by the fluorescent X-ray analysis with high precision.

(Third Example of Embodiment 1)

Figure 9A:
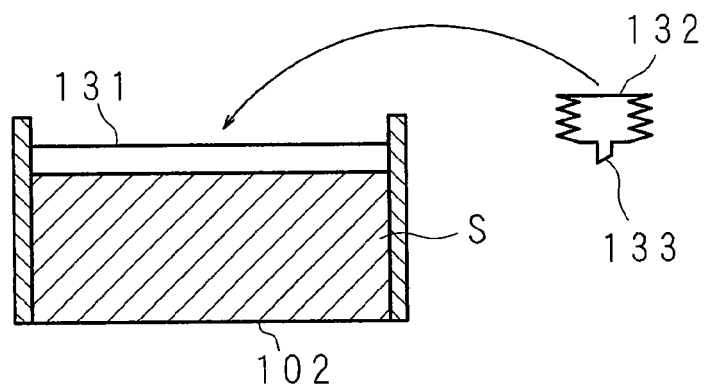
FIGS. 9A and 9B are schematic cross-sectional views of a sample cell according to a third example of Embodiment 1.
Figure 9B:
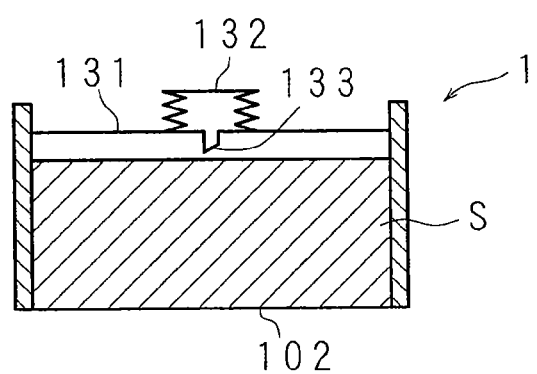

In a third example of Embodiment 1, the structure of the fluorescent X-ray analyzer is the same as that in the first example, but the structure of the sample cell 1 is different. FIGS. 9A and 9B are schematic cross-sectional views of the sample cell 1 according to the third example of Embodiment 1. A cup end surface 131 of the sample cup constituting the sample cell 1 is formed flat. In the present example, as illustrated in FIG. 9A, a bellows member 132 formed into a bellows shape having a hollow thereinside as a whole is attached to the cup end surface 131. The bellows member 132 has a sticking part 133 that may be stuck into and passed through the cup end surface 131, and is attached to the cup end surface 131 using the sticking part 133. FIG. 9B illustrates a state where the bellows member 132 is attached to the cup end surface 131, and the sticking part 132 is stuck into and passed through the cup end surface 131, and the bellows member 132 is thereby attached to the cup end surface 131. The bellows member 132 is fixed to the cup end surface 131 using an adhesive or the like. The sticking part 133 is formed into an opened hollow tubular shape coupled to the hollow inside the bellows member 132. Consequently, the sticking part 133 is passed through the cup end surface 131, and the space inside the sample cell 1 and the hollow inside the bellows member 132 are coupled to each other via the sticking part 133. The bellows member 132 is deformed into a shape that is extended outwardly of the sample cell 1, and the internal capacity of the sample cell 1 including the hollow inside the bellows member 132 is thereby increased. The bellows member 132 functions as the deforming part in the present invention.

FIGS. 10A to 10D are schematic cross-sectional views illustrating usage of the sample cell 1 according to the third example of Embodiment 1. First, as illustrated in FIG. 10A, the sample cup is put on the cell inner frame 101 from above, and the fluid sample S is injected from the opening portion of the sample cup into the sample cup with the cup end surface 131 disposed on the lower side. Next, as illustrated in FIG. 10B, the opening portion of the sample cup is covered with the X-ray transmission sheet 102 and the cell outer frame 103 is externally fitted thereon, whereby the fluid sample S is contained. Subsequently, the sample cell 1 is turned upside down and, as illustrated in FIG. 10C, the bellows member 132 is further attached to the cup end surface 131 with the X-ray transmission sheet 102 serving as the bottom surface and the cup end surface 131 disposed on the upper side, whereby the sample cell 1 is assembled. The sample cell 1 containing the fluid sample S therein is placed on the cell holder 2, and the fluorescent X-ray analysis is performed. In this state, the bellows member 132 is contracted.

When the fluid sample S is volatilized with the passage of time to increase the internal pressure of the sample cell 1 during the execution of the fluorescent X-ray analysis, the internal pressure of the bellows member 132 is also increased through the sticking part 133, and the bellows member 132 is extended in response to the increase in pressure. As illustrated in FIG. 10D, the bellows member 132 is deformed while being extended outwardly of the sample cell 1, and the internal capacity of the sample cell 1 is thereby increased. The internal capacity of the sample cell 1 is increased to relieve the increase in the internal pressure of the sample cell 1, and hence the expansion of the X-ray transmission sheet 102 due to the increase in pressure is prevented.

As has been described above, in the fluorescent X-ray analyzer using the sample cell 1 according to the third example as well, when the fluid sample S is volatilized inside the sample cell 1 to increase the internal pressure of the sample cell 1, the X-ray transmission sheet 102 as the window part through which the primary X-rays and the fluorescent X-rays are transmitted is not expanded. Consequently, the distance between the fluid sample S and the X-ray detector 4 detecting the fluorescent X-rays is not fluctuated, and the intensities of the fluorescent X-rays detected by the X-ray detector 4 are not fluctuated as well, and hence it becomes possible to perform the element analysis of the fluid sample S by the fluorescent X-ray analysis with high precision.

(Fourth Example of Embodiment 1)

Figure 11A:
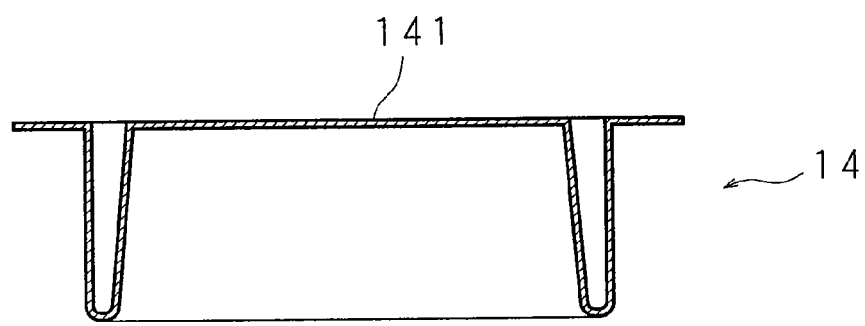
FIGS. 11A and 11B are schematic cross-sectional views of a sample cup according to a fourth example of Embodiment 1.
Figure 11B:
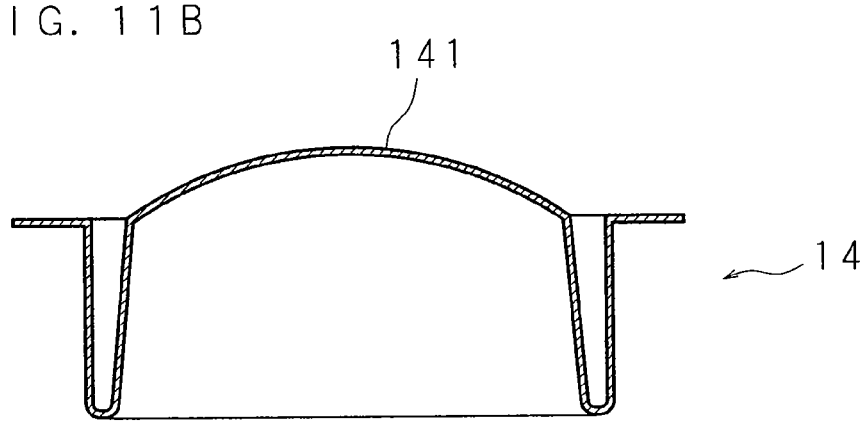

In a fourth example of Embodiment 1, the structure of the fluorescent X-ray analyzer is the same as that in the first example, but the shape of the sample cup of the sample cell 1 is different. FIGS. 11A and 11B are schematic cross-sectional views of a sample cup 14 according to the fourth example of Embodiment 1. A cup end surface 141 of the sample cup 14 is formed flat by using a sheet having elasticity such as a thin rubber film or the like. Since the cup end surface 141 has elasticity, when a force is applied to the cup end surface 141 from the inside of the sample cup 14, the cup end surface 141 is deformed outwardly of the sample cup 14. FIG. 11A illustrates a state where the cup end surface 141 is flat, while FIG. 11B illustrates a state where the cup end surface 141 is deformed. When the pressure from the inside of the sample cup 14 is increased, as illustrated in FIG. 11B, the cup end surface 141 is expanded outwardly of the sample cup 14, and the internal capacity of the sample cup 14 is thereby increased. Since the cup end surface 141 is formed of the sheet having elasticity in this manner, when the pressure from the inside of the sample cup 14 is normal, the cup end surface 141 is flat, as illustrated in FIG. 11A. On the other hand, when the pressure from the inside of the sample cup 14 is increased, the cup end surface 141 is deformed into a shape that is expanded outwardly of the sample cup 14, as illustrated in FIG. 11B. The cup end surface 141 is deformed into the shape that is expanded outwardly of the sample cup 14, and the internal capacity of the sample cup 14, i.e., the internal capacity of the sample cell 1 is thereby increased. The cup end surface 141 functions as the deforming part in the present invention. The structure of the sample cell 1 other than the sample cup 14 is the same as that in the first example.

Figure 12A:
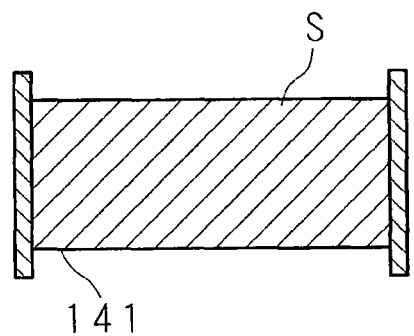
FIGS. 12A to 12D are schematic cross-sectional views illustrating usage of a sample cell according to the fourth example of Embodiment 1.
Figure 12B:
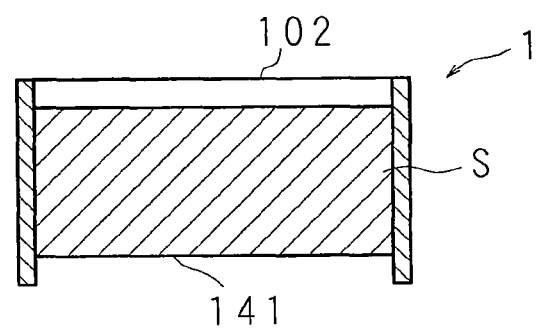
Figure 12C:
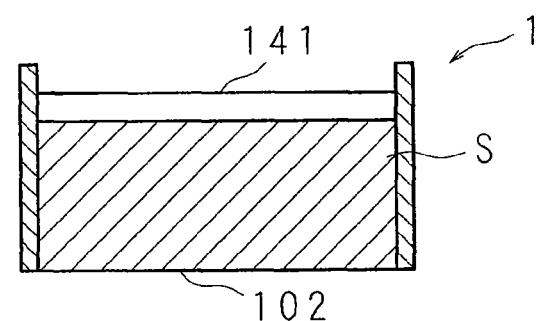

FIGS. 12A to 12D are schematic cross-sectional views illustrating usage of the sample cell 1 according to the fourth example of Embodiment 1. First, as illustrated in FIG. 12A, the sample cup 14 is put on the cell inner frame 101 from above, and the fluid sample S is injected from the opening portion of the sample cup 14 into the sample cup 14 with the cup end surface 141 disposed on the lower side. Next, as illustrated in FIG. 12B, the opening portion of the sample cup 14 is covered with the X-ray transmission sheet 102, and the cell outer frame 103 is externally fitted thereon. In this manner, the sample cell 1 is assembled, and the fluid sample S is contained. Subsequently, the sample cell 1 is turned upside down, the sample cell 1 is placed on the cell holder 2 with the X-ray transmission sheet 102 serving as the bottom surface and the cup end surface 141 disposed on the upper side as illustrated in FIG. 12C, and the fluorescent X-ray analysis is performed. In this state, the cup end surface 141 is flat.

Figure 12D:
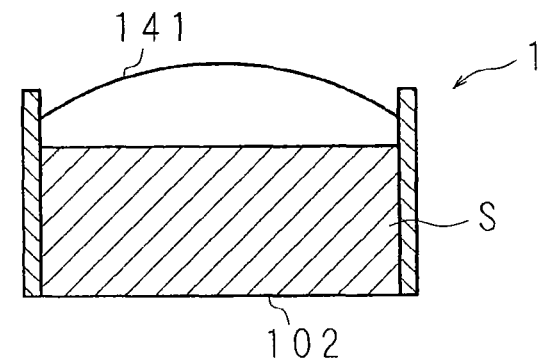

When the fluid sample S is volatilized with the passage of time to increase the internal pressure of the sample cell 1 during the execution of the fluorescent X-ray analysis, the cup end surface 141 is expanded in response to the increase in pressure. As illustrated in FIG. 12D, the cup end surface 141 is deformed while being expanded outwardly of the sample cell 1, and the internal capacity of the sample cell 1 is thereby increased. The internal capacity of the sample cell 1 is increased to relieve the increase in the internal pressure of the sample cell 1, and hence the expansion of the X-ray transmission sheet 102 due to the increase in pressure is prevented.

As has been described above, in the fluorescent X-ray analyzer using the sample cell 1 according to the fourth example as well, when the fluid sample S is volatilized inside the sample cell 1 to increase the internal pressure of the sample cell 1, the X-ray transmission sheet 102 as the window part through which the primary X-rays and the fluorescent X-rays are transmitted is not expanded. Consequently, the distance between the fluid sample S and the X-ray detector 4 detecting the fluorescent X-rays is not fluctuated, and the intensities of the fluorescent Rays detected by the X-ray detector 4 are not fluctuated as well, and hence it becomes possible to perform the element analysis of the fluid sample S by the fluorescent X-ray analysis with high precision.

(Fifth Example of Embodiment 1)

In a fifth example of Embodiment 1, the structure of the fluorescent X-ray analyzer is the same as that in the first example, but the shape of the sample cup of the sample cell 1 is different. FIGS. 13A and 13B are schematic cross-sectional views of a sample cup 15 according to the fifth example of Embodiment 1. A cup end surface 151 of the sample cup 15 is formed of a deformable sheet, and is formed by convexly deforming a sheet larger than a cross-sectional area of the sample cup 15 inwardly of the sample cup 15 in advance. When a force is applied to the cup end surface 151 from the inside of the sample cup 15, the cup end surface 151 is deformed outwardly of the sample cup 15. FIG. 13A illustrates a state where the cup end surface 151 is convexly deformed inwardly of the sample cup 15, while FIG. 13B illustrates a state where the cup end surface 151 is deformed outwardly of the sample cup 15. When the pressure from the inside of the sample cup 15 is increased, the cup end surface 151 is deformed outwardly of the sample cup 15. For example, the cup end surface 151 is convexly deformed outwardly of the sample cup 15, as illustrated in FIG. 13B. The cup end surface 151 is deformed outwardly of the sample cup 15, and the internal capacity of the sample cup 15 is thereby increased.

Since the cup end surface 151 is formed of the deformable sheet larger than the cross-sectional area of the sample cup 15 in this manner, when the pressure from the inside of the sample cup 15 is normal, the cup end surface 151 is convexly deformed inwardly of the sample cup 15, as illustrated in FIG. 13A. On the other hand, when the pressure from the inside of the sample cup 15 is increased, the cup end surface 151 is deformed so as to be expanded outwardly of the sample cup 15, as illustrated in FIG. 13B. The cup end surface 151 is deformed outwardly of the sample cup 15, and the internal capacity of the sample cup 15, i.e., the internal capacity of the sample cell 1 is thereby increased. The cup end surface 151 functions as the deforming part in the present invention. The structure of the sample cell 1 other than the sample cup 15 is the same as that in the first example.

Figure 14A:
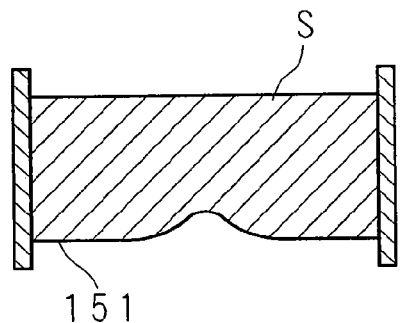
FIGS. 14A to 14D are schematic cross-sectional views illustrating usage of a sample cell according to the fifth example of Embodiment 1.
Figure 14B:
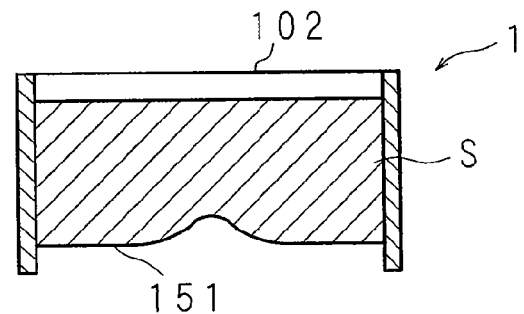
Figure 14C:
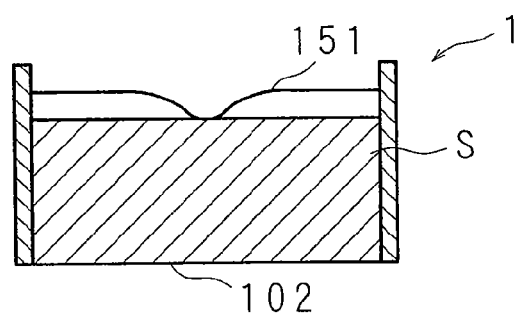

FIGS. 14A to 14D are schematic cross-sectional views illustrating usage of the sample cell 1 according to the fifth example of Embodiment 1. First, as illustrated in FIG. 14A, the sample cup 15 is put on the cell inner frame 101 from above, and the fluid sample S is injected from the opening portion of the sample cup 15 into the sample cup 15 with the cup end surface 151 disposed on the lower side. Next, as illustrated in FIG. 14B, the opening portion of the sample cup 15 is covered with the X-ray transmission sheet 102, and the cell outer frame 103 is externally fitted thereon. In this manner, the sample cell 1 is assembled, and the fluid sample S is contained. Subsequently, as illustrated in FIG. 14C, the sample cell 1 is turned upside down, the sample cell 1 is placed on the cell holder 2 with the X-ray transmission sheet 102 serving as the bottom surface and the cup end surface 151 disposed on the upper side, and the fluorescent X-ray analysis is performed. In this state, the cup end surface 151 is convexly deformed inwardly of the sample cell 1.

Figure 14D:
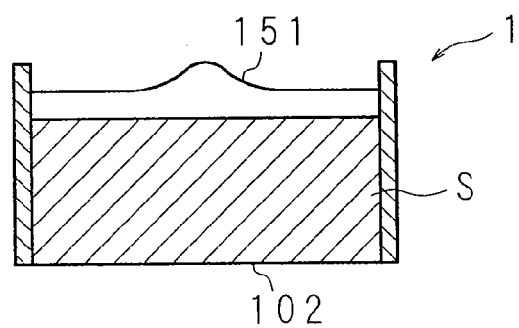

When the fluid sample S is volatilized with the passage of time to increase the internal pressure of the sample cell 1 during the execution of the fluorescent X-ray analysis, the cup end surface 151 is deformed in response to the increase in pressure. As illustrated in FIG. 14D, the cup end surface 151 is deformed while being expanded outwardly of the sample cell 1, and the internal capacity of the sample cell 1 is thereby increased. The internal capacity of the sample cell 1 is increased to relieve the increase in the internal pressure of the sample cell 1, and hence the expansion of the X-ray transmission sheet 102 due to the increase in pressure is prevented.

As has been described above, in the fluorescent X-ray analyzer using the sample cell 1 according to the fifth example as well, when the fluid sample S is volatilized inside the sample cell 1 to increase the internal pressure of the sample cell 1, the X-ray transmission sheet 102 as the window part through which the primary X-rays and the fluorescent X-rays are transmitted is not expanded. Consequently, the distance between the fluid sample S and the X-ray detector 4 detecting the fluorescent X-rays is not fluctuated, and the intensities of the fluorescent X-rays detected by the X-ray detector 4 are not fluctuated as well, and hence it becomes possible to perform the element analysis of the fluid sample S by the fluorescent X-ray analysis with high precision.

Although the first to fifth examples described above have described configurations in which various deforming parts that are deformed in response to the increase in the internal pressure of the sample cell 1 are provided in the cup end surface, the configuration is not limited thereto, and the sample cell 1 of the present invention may have a configuration in which the deforming part is provided in a portion other than the cup end surface such as a side surface or the like as long as the portion does not correspond to the X-ray transmission sheet 102.

(Sixth Example of Embodiment 1)

In a sixth example of Embodiment 1, the structure of the fluorescent X-ray analyzer is the same as that in the first example, but the shape of the sample cup of the sample cell 1 is different. FIGS. 15A and 15B are schematic cross-sectional views of a sample cup 16 according to the sixth example of Embodiment 1. A cup end surface 161 of the sample cup 16 is formed flat. In addition, as illustrated in FIG. 15A, the cup end surface 161 is formed with two holes 162 and 163 connected to the space inside the sample cup 16. As illustrated in FIG. 15B, a plug 164 is attached to the hole 162, and a plug 165 is attached to the hole 163, whereby the holes 162 and 163 are sealed. The structure of the sample cell 1 other than the sample cup 16 is the same as that in the first example.

Figure 16A:
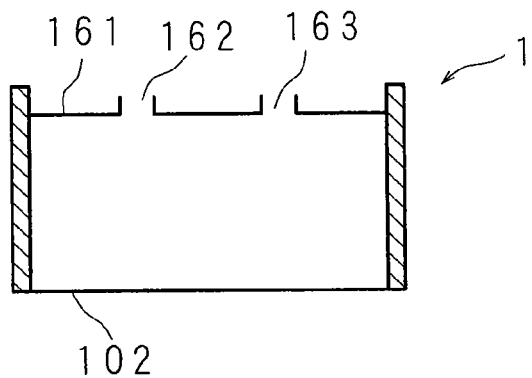
FIGS. 16A to 16C are schematic cross-sectional views illustrating usage of a sample cell according to the sixth example of Embodiment 1.
Figure 16B:
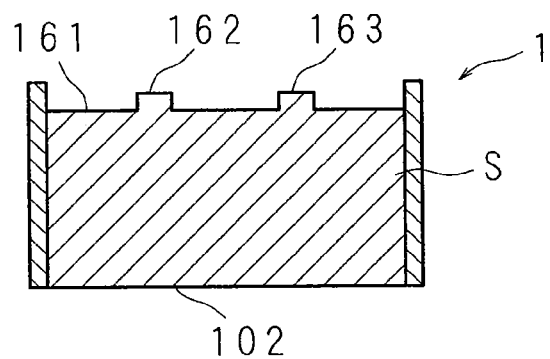
Figure 16C:
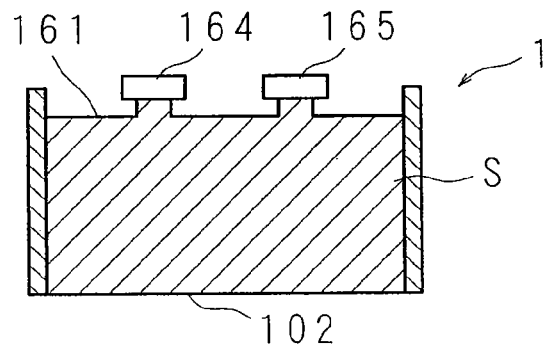

FIGS. 16A to 16C are schematic cross-sectional views illustrating usage of the sample cell 1 according to the sixth example of Embodiment 1. First, as illustrated in FIG. 16A, the sample cup 16 is put on the cell inner frame 101, the opening portion of the sample cup 16 is covered with the X-ray transmission sheet 102, and the cell outer frame 103 is externally fitted thereon, whereby the sample cell 1 is assembled, and the X-ray transmission sheet 102 is used as the bottom surface. Next, as illustrated in FIG. 16B, the fluid sample S is injected from either of the holes 162 and 163, and the space inside the sample cell 1 is fully filled with the fluid sample S. At this point, one of the holes 162 and 163 serves as an inlet for the fluid sample S, and the other one serves as an outlet for the air. The fluid sample S having spilled on the cup end surface 161 from the hole 162 or 163 when the space has been fully filled with the fluid sample S is removed by wiping or sucking. Subsequently, as illustrated in FIG. 16C, the plugs 164 and 165 are attached to the holes 162 and 163 to seal the holes 162 and 163. By sealing the holes 162 and 163 using the plugs 164 and 165, the sample cell 1 is fully filled with the fluid sample S, and the air is no longer present therein. The fluid sample S having spilled on the cup end surface 161 when the plugs 164 and 165 have been attached is removed. It is to be noted that a frame surrounding the holes 162 and 163 may be provided on the cup end surface 161 such that the fluid sample S having overflowed from the holes 162 and 163 does not flow out of the cup end surface 161. In addition, the number of holes formed in the cup end surface 161 is not limited to two, and the sample cup 16 may have a configuration in which one hole capable of injection of the fluid sample S and ejection of the air alone and simultaneously is formed in the cup end surface 161, or a configuration in which three or more holes are formed in the cup end surface 161.

The sample cell 1 fully filled with the fluid sample S is placed on the cell holder 2 with the X-ray transmission sheet 102 serving as the bottom surface, and the fluorescent X-ray analysis is performed. Even when the fluid sample S is about to be volatilized with the passage of time during the execution of the fluorescent X-ray analysis, since the sample cell 1 is sealed and no air is present inside the sample cell 1, the fluid sample S may not be volatilized. Consequently, the internal pressure of the sample cell 1 is not increased, and hence the expansion of the X-ray transmission sheet 102 due to the increase in pressure is prevented.

As has been described above, in the fluorescent X-ray analyzer using the sample cell 1 according to the sixth example, since the fluid sample S is not volatilized inside the sample cell 1 to increase the internal pressure of the sample cell 1, the X-ray transmission sheet 102 as the window part through which the primary X-rays and the fluorescent X-rays are transmitted is not expanded. Consequently, the distance between the fluid sample S and the X-ray detector 4 detecting the fluorescent X-rays is not fluctuated, and the intensities of the fluorescent X-rays detected by the X-ray detector 4 are not fluctuated as well, and hence it becomes possible to perform the element analysis of the fluid sample S by the fluorescent X-ray analysis with high precision.

(Seventh Example of Embodiment 1)

Figure 17A:
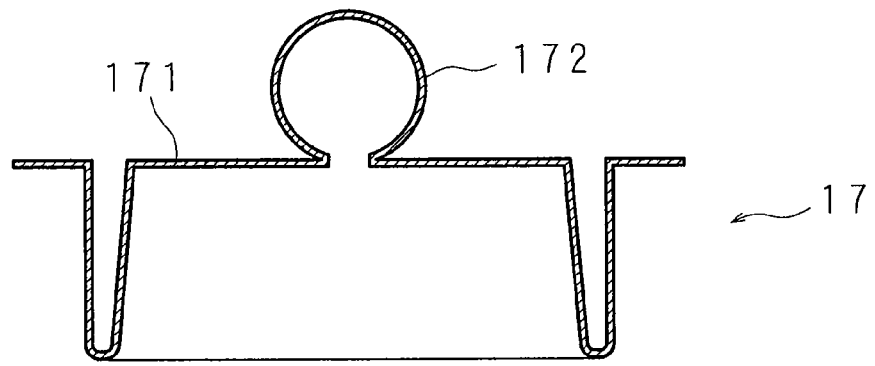
FIGS. 17A and 17B are schematic cross-sectional views of a sample cup according to a seventh example of Embodiment 1.
Figure 17B:
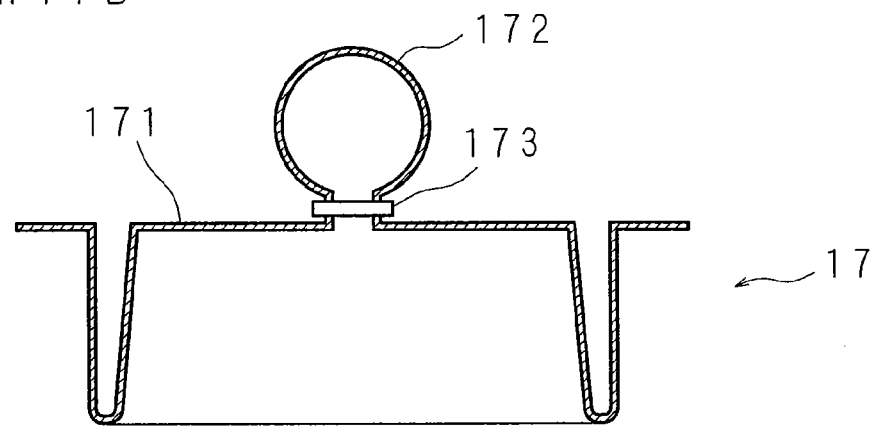

In a seventh example of Embodiment 1, the structure of the fluorescent X-ray analyzer is the same as that in the first example, but the shape of the sample cup of the sample cell 1 is different. FIGS. 17A and 17B are schematic cross-sectional views of a sample cup 17 according to the seventh example of Embodiment 1. A cup end surface 171 of the sample cup 17 is provided with an expandable balloon part 172 formed of a thin rubber material. As illustrated in FIG. 17A, the balloon part 172 is formed to be expandable outwardly of the sample cup 17, and the hollow inside the balloon part 172 is coupled to the space inside the sample cell 1 formed by the sample cup 17. Further, as illustrated in FIG. 17B, it is possible to bind a base of the balloon part 172, i.e., a portion where the balloon part 172 and the cup end surface 171 are connected to each other using a binding member 173 such as a clip or an elastic cord. In the state where the base of the balloon part 172 is bound using the binding member 173, gas and liquid may not move between the space inside the balloon part 172 and the space inside the sample cell 1. The structure of the sample cell 1 other than the sample cup 17 is the same as that in the first example.

Figure 18A:
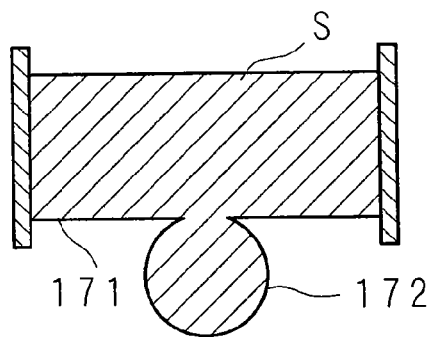
FIGS. 18A to 18D are schematic cross-sectional views illustrating usage of a sample cell according to the seventh example of Embodiment 1.
Figure 18B:
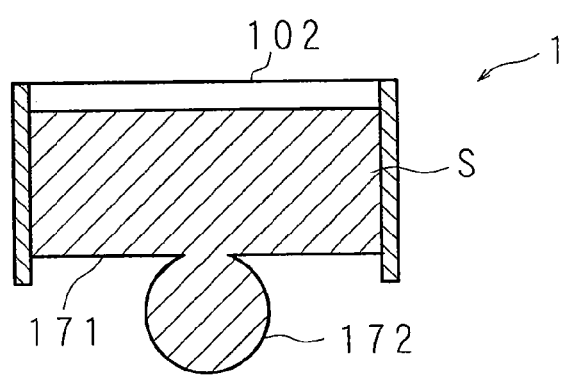
Figure 18C:
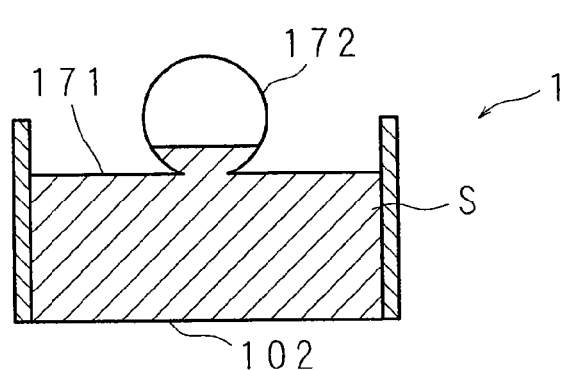
Figure 18D:
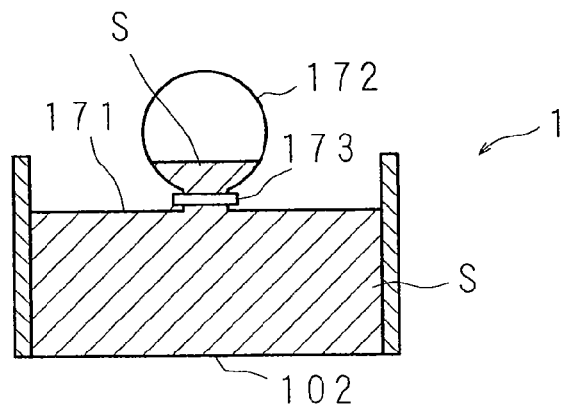

FIGS. 18A to 18D are schematic cross-sectional views illustrating usage of the sample cell 1 according to the seventh example of Embodiment 1. First, as illustrated in FIG. 18A, the sample cup 17 is put on the cell inner frame 101 from above, and the fluid sample S is injected from the opening portion of the sample cup 17 into the sample cup 17 with the cup end surface 171 disposed on the lower side. Next, as illustrated in FIG. 18B, the opening portion of the sample cup 17 is covered with the X-ray transmission sheet 102, and the cell outer frame 103 is externally fitted thereon. In this manner, the sample cell 1 is assembled, and the fluid sample S is contained. Subsequently, the sample cell 1 is turned upside down, and the X-ray transmission sheet 102 is used as the bottom surface and the cup end surface 171 is disposed on the upper side, as illustrated in FIG. 18C. The amount of the fluid sample S is adjusted in advance such that the fluid sample S enters into the balloon part 172 at this point. Then, as illustrated in FIG. 18D, the base of the balloon part 172 is bound using the binding member 173. In this state, the sample cell 1 is fully filled with the fluid sample S, and the fluid sample S and the air are present inside the balloon part 172. The binding member 173 prevents the movement of substances between the inside of the sample cell 1 and the balloon part 172.

The sample cell 1 in the state illustrated in FIG. 18D is placed on the cell holder 2 with the X-ray transmission sheet 102 serving as the bottom surface, and the fluorescent X-ray analysis is performed. When the fluid sample S is about to be volatilized with the passage of time during the execution of the fluorescent X-ray analysis, the fluid sample S may be volatilized inside the balloon part 172, but the fluid sample S may not be volatilized inside the sample cell 1 because the sample cell 1 is fully filled with the fluid sample S so that no air is present therein. Although the internal pressure is increased with the volatilization of the fluid sample S inside the balloon part 172, since the movement of the fluid sample S and the air from the inside of the balloon part 172 to the inside of the sample cell 1 is prevented by the binding member 173, the internal pressure of the sample cell 1 is not increased. Consequently, the expansion of the X-ray transmission sheet 102 due to the increase in pressure is prevented.

As has been described above, in the fluorescent X-ray analyzer using the sample cell 1 according to the seventh example, since the fluid sample S is not volatilized inside the sample cell 1 to increase the internal pressure of the sample cell 1, the X-ray transmission sheet 102 as the window part through which the primary X-rays and the fluorescent X-rays are transmitted is not expanded. Consequently, the distance between the fluid sample S and the X-ray detector 4 detecting the fluorescent X-rays is not fluctuated, and the intensities of the fluorescent X-rays detected by the X-ray detector 4 are not fluctuated as well, and hence it becomes possible to perform the element analysis of the fluid sample S by the fluorescent X-ray analysis with high precision.

(Embodiment 2)

A description will be given of Embodiment 2 characterized in a cell holder on which the sample cell is placed, and a sample cell assembly instrument used when the sample cell is assembled.

Figure 19:
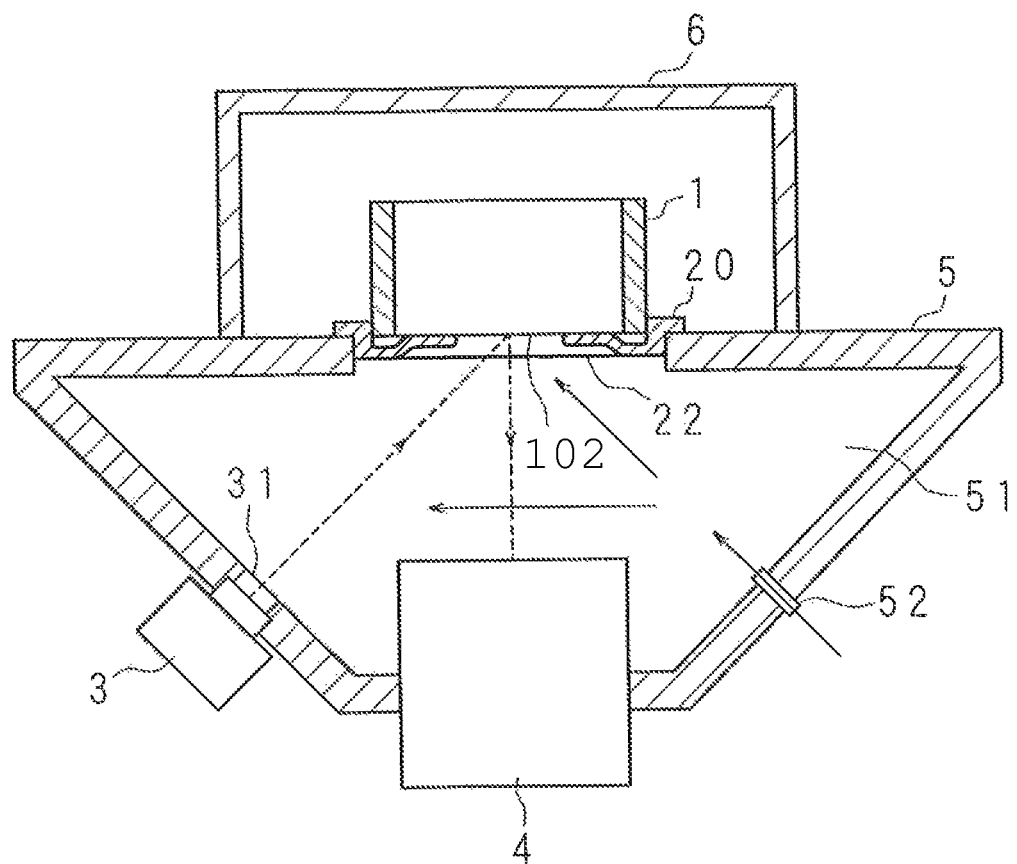
FIG. 19 is a schematic view illustrating a structure of a fluorescent X-ray analyzer according to Embodiment 2.

FIG. 19 is a schematic view illustrating a structure of a fluorescent X-ray analyzer according to Embodiment 2. The structure of the fluorescent X-ray analyzer is the same as that of the above-described fluorescent X-ray analyzer according to Embodiment 1, and the description of parts that are the same as those in FIG. 1 will be omitted by using like reference numerals to designate like parts.

The opening portion is formed in the center of the flat surface of the upper portion of the housing 5, and a cell holder 20 is attached to be fitted in the opening portion. Further, the sample cell (sample cell for fluorescent X-ray analysis) 1 in which the sample to be analyzed is contained is placed on the cell holder 20. The cell holder 20 and the sample cell 1 placed on the cell holder 20 are covered with the cover 6. The cell holder 20 is provided with the X-ray transmission sheet 22 that allows transmission of the X-rays.

Figure 20:
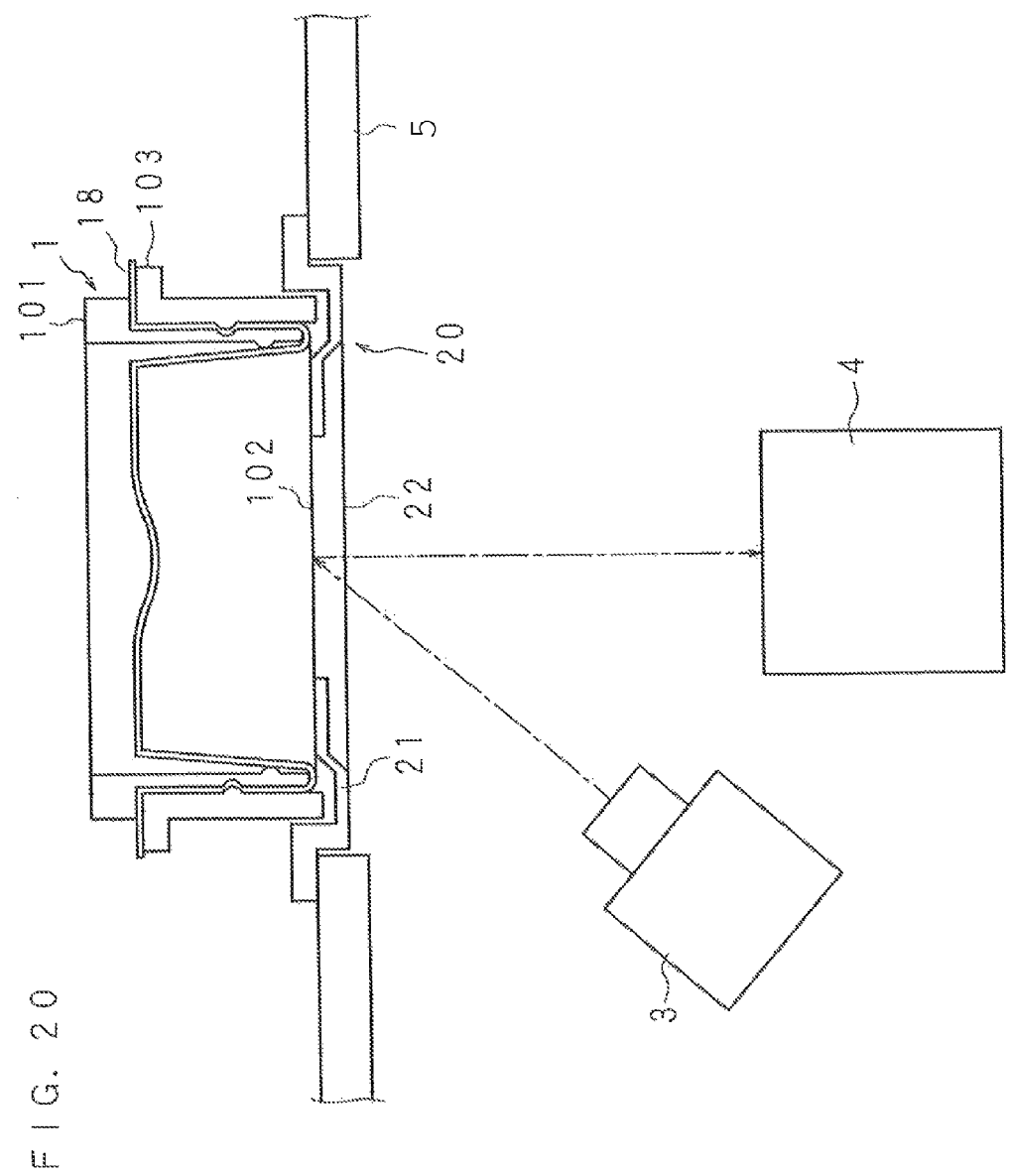
FIG. 20 is a cross-sectional view illustrating structures of a sample cell and a cell holder.

FIG. 20 is a cross-sectional view illustrating structures of the sample cell 1 and the cell holder 20. FIG. 21 is an exploded perspective view illustrating the structure of the sample cell 1. Similarly to Embodiment 1, the sample cell 1 includes the cell inner frame 101, a sample cup 18, the cell outer frame 103, and the X-ray transmission sheet 102.

The sample cup 18 is formed by bending a sheet such as a flexible plastic film or the like. The sample cup 18 has a cylindrical sample containing part 182 having a cup end surface 181 on one end and an opening portion on the other end, a cylindrical surrounding part 183 that is coupled to the opening portion of the sample containing part 182 and provided at a predetermined distance from an outer circumferential surface of the sample containing part 182 so as to surround the outer circumferential surface of the sample containing part 182, and a flange part 184 provided completely around an outer circumferential surface in an end portion of the surrounding part 183. In addition, as will be described later, the cup end surface 181 is deformable inwardly of the sample cell 1.

It is to be noted that, since the structures of the cell inner frame 101, the X-ray transmission sheet 102, and the cell outer frame 103, and the relationships between the individual parts mentioned above and the sample cup 18 are the same as those in Embodiment 1 described above, the description thereof will be omitted by using like reference numerals to designate like parts.

Figure 22:
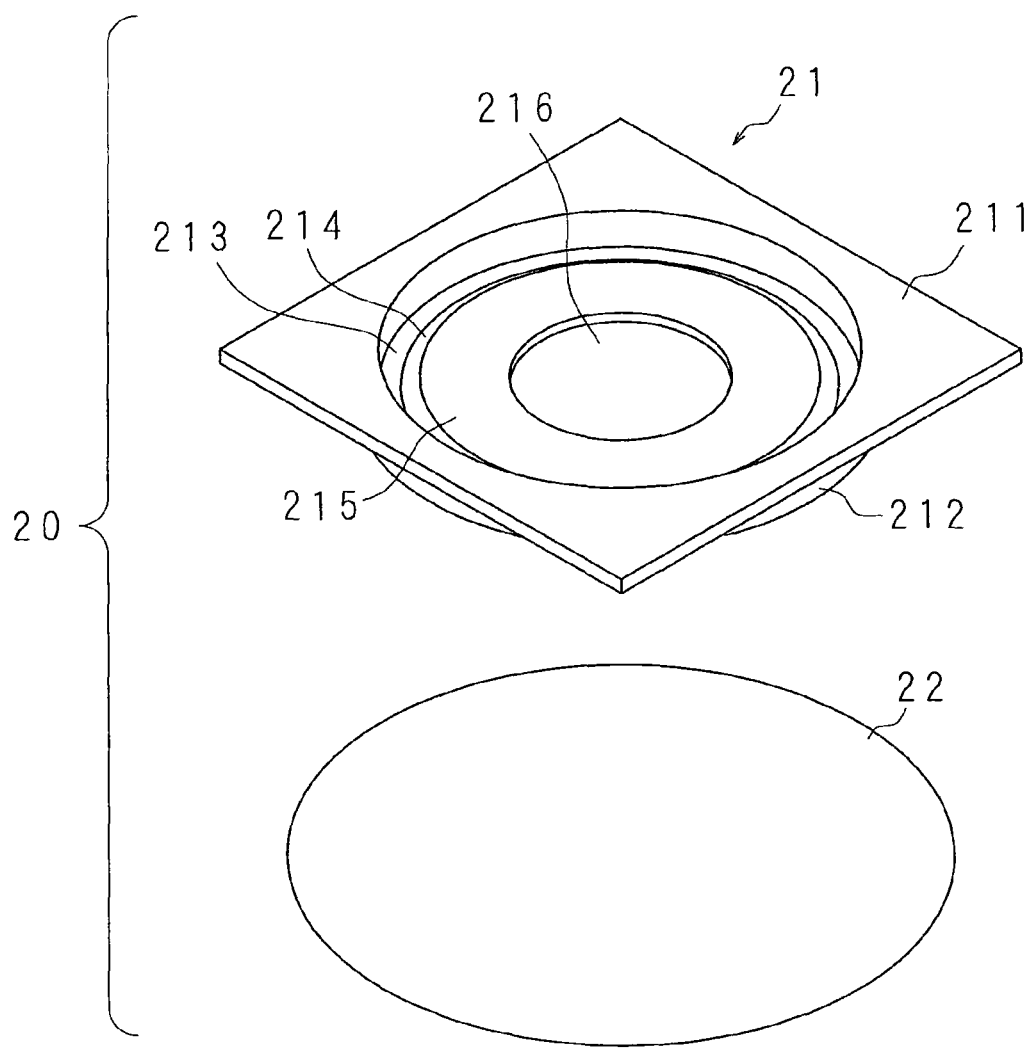
FIG. 22 is an exploded perspective view illustrating the structure of the cell holder.

FIG. 22 is an exploded perspective view illustrating the structure of the cell holder 20. The cell holder 20 includes a cell supporting member 21 and the X-ray transmission sheet 22. The cell supporting member 21 is made of a metal such as copper or aluminum, and is provided with a disk-like bottom plate part 213 formed with an opening portion 216 in the center on one end of a cylinder having a circumferential wall part 212, and a flange part 211 on the other end thereof. The inner diameter of the circumferential wall part 212 is larger than the outer diameter of the cylindrical portion of the cell outer frame 103 of the sample cell 1, and the height of the circumferential wall part 212 is sufficiently lower than the height of the sample cell 1 in an axial direction.

In addition, the cell supporting member 21 has a supporting part 214 provided completely around the circumference of the opening portion 216 to obliquely and upwardly project toward the inside of the opening portion 216. That is, the supporting part 214 is in a cylindrical shape (generally circular truncated cone shape) reducing in diameter upwardly and, in an edge portion (upper end portion) of the supporting part 214, formed is an annular, horizontal, and smooth supporting plane 215. The outer diameter of the supporting plane 215 is smaller than the diameter of the opening portion of the sample cup 18 of the sample cell 1. It is to be noted that, although the supporting part 214 illustrated in the drawing is in the cylindrical shape reducing in diameter upwardly, the shape is not limited thereto, and the supporting part 214 may be formed substantially vertical.

The X-ray transmission sheet 22 is in a shape of a substantially circular thin sheet having a diameter larger than the outer diameter of the cell supporting member 21, and is the same as the X-ray transmission sheet 102 of the sample cell 1. The X-ray transmission sheet 22 is set on the bottom surface of the cell supporting member 21 by a method described later, and is fixed from the outside using an annular elastic member such as an O ring or the like to be attached to the cell supporting member 21. The X-ray transmission sheet 22 attached to the cell supporting member 21 covers and closes the opening portion 216. By attaching the X-ray transmission sheet 22 to the cell supporting member 21, the cell holder 20 is assembled. By attaching the assembled cell holder 20 to the opening portion of the housing 5 using a bolt or the like, the measurement chamber 51 of the fluorescent X-ray analyzer is sealed.

Figure 23:
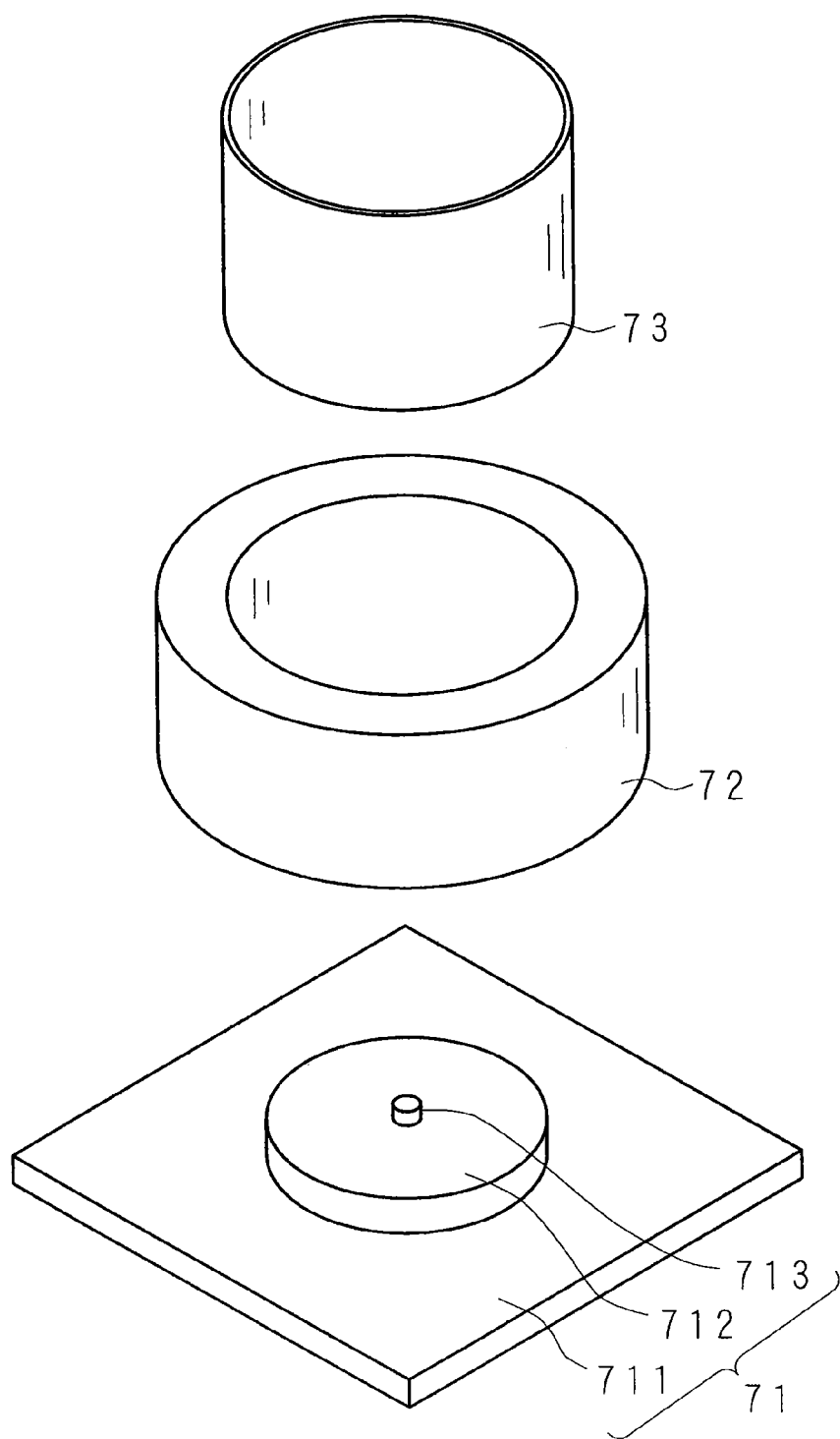
FIG. 23 is a perspective view illustrating a structure of a sample cell assembly instrument of the present invention.

Next, a description will be given of the sample cell assembly instrument of the present invention for assembling the sample cell 1. FIG. 23 is a perspective view illustrating the structure of the sample cell assembly instrument of the present invention. The sample cell assembly instrument includes a sample cup placing stand 71 for supporting the sample cup 18 during the assembly of the sample cell 1, a sheet placing instrument 72 for supporting the X-ray transmission sheet 102, and an outer frame fitting instrument 73 used to fit the cell outer frame 103 on the sample cup 18. The sample cup placing stand 71, the sheet placing instrument 72, and the outer frame fitting instrument 73 are formed of a metal such as brass, aluminum, or the like. It is to be noted that the sheet placing instrument 72 may also be formed of a resin.

In the sample cup placing stand 71, a column part (positioning part) 712 is provided on an upper surface of a flat plate part 711 formed into a flat plate-like shape, and a projection part (pushing-up part) 713 is formed on a top surface of the column part 712. An area of the flat plate part 711 is sufficiently large enough to have the sample cell 1 and the sheet placing instrument 72 placed thereon. The outer diameter of the column part 712 is slightly smaller than the inner diameter of the flange part 101a of the cell inner frame 101, and is a size that allows the flange part 101a of the cell inner frame 101 to be externally fitted on the column part 712 to position the sample cup 18 when the sample cup 18 in which the cell inner frame 101 is fitted is placed on the sample cup placing stand 71 with the opening portion disposed on the upper side. The height of the column part 712 is lower than the height of the flange part 101a of the cell inner frame 101. The projection part 713 is provided in a substantially center of the top surface of the column part 712. The height of the projection part 713 when combined with the height of the column part 712 is slightly higher than the height of the flange part 101a of the cell inner frame 101, and is a height with which the cup end surface 181 of the sample cup 18 is pushed to be deformed by the projection part 713 when the sample cup 18 in which the cell inner frame 101 is fitted is placed on the sample cup placing stand 71 with the opening portion disposed on the upper side. It is to be noted that the sample cup placing stand 71 may have a shape formed with a groove matching the shape of the flange part 101a of the inner cell frame 101 for positioning the sample cup 18 instead of having the column part 712.

The sheet placing instrument 72 is in a cylindrical shape with both ends opened. The inner diameter of the sheet placing instrument 72 is larger than each of the outer diameter of the flange part 103a of the cell outer frame 103 and the outer diameter of the flange part 184 of the sample cup 18, and is smaller than the outer diameter of the X-ray transmission sheet 102. The outer diameter of the sheet placing instrument 72 is a size that allows the X-ray transmission sheet 102 to be placed on the upper surface of the sheet placing instrument 72. It is to be noted that the outer shape of the sheet placing instrument 72 may be in a shape other than the circular shape such as a polygonal shape or the like. The height of the sheet placing instrument 72 is higher than the height of the sample cup 18 in which the cell inner frame 101 is fitted. That is, when the sample cup 18 in which the cell inner frame 101 is fitted is placed on the sample cup placing stand 71, and the sheet placing instrument 72 is further placed thereon, the sheet placing instrument 72 surrounds the sample cup 18, and the height thereof is higher than that of the sample cup 18. In addition, both end surfaces of the sheet placing instrument 72 are in parallel with each other, and are orthogonal to the axis thereof so as to be able to place the X-ray transmission sheet 102 on the sheet placing instrument 72 placed on the sample cup placing stand 71. It is to be noted that the sample cup placing stand 71 may be in a shape further formed with a column part or a groove for positioning the sheet placing instrument 72 when the sheet placing instrument 72 is placed thereon.

The outer frame fitting instrument 73 is formed into a cylindrical shape with both ends opened. The inner diameter of the outer frame fitting instrument 73 is smaller than the outer diameter of the flange part 103a of the cell outer frame 103, slightly larger than the outer diameters of the other portions of the cell outer frame 103, and is formed into a size that allows the cell outer frame 103 to be inserted from the side opposite to the side of the flange part 103a to be fitted in the outer frame fitting instrument 73. The outer diameter of the outer frame fitting instrument 73 is small than the inner diameter of the sheet placing instrument 72, and is formed into a size that allows the outer frame fitting instrument 73 to be inserted into the sheet placing instrument 72. Furthermore, the height of the outer frame fitting instrument 73 is higher than that of the cell outer frame 103. It is to be noted that the outer frame fitting instrument 73 may have a flange part so as to be easily held, and may also be partially formed with a slit such that the cell outer frame 103 is easily removed after the cell outer frame 103 is fitted on the sample cup 18.

Figure 24A:
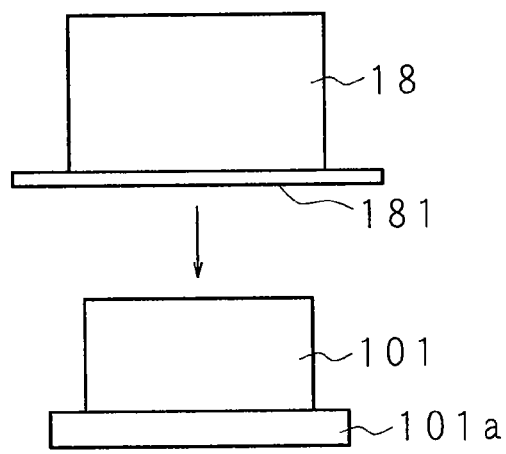
FIGS. 24A and 24B are explanatory views for explaining a method for assembling the sample cell when viewed from a front side.
Figure 24B:
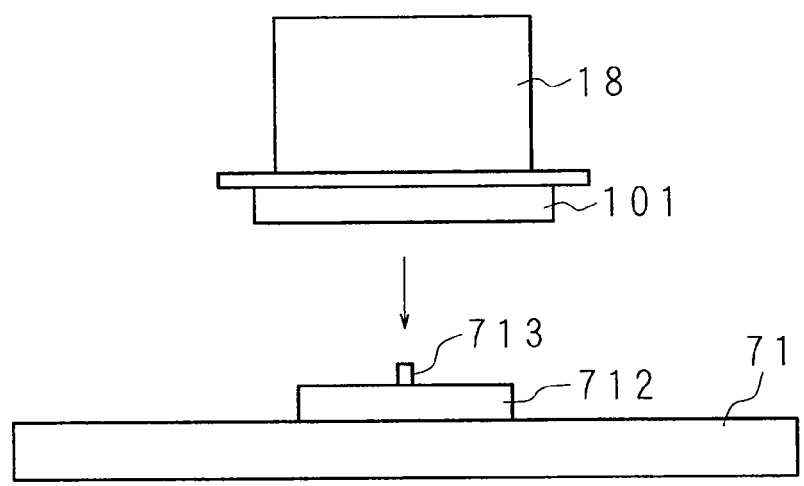

Next, a description will be given of a method for assembling the sample cell 1 by using the sample cell assembly instrument of the present invention. FIGS. 24 to 28 are explanatory views for explaining the method for assembling the sample cell 1 when viewed from the front side. First, as illustrated in FIG. 24A, the sample cup 18 is put from above on the cell inner frame 101 with the flange part 101a disposed on the lower side. In this state, the cup end surface 181 is disposed on the lower side, and the cell inner frame 101 is fitted in the sample cup 18. Next, as illustrated in FIG. 24B, the sample cup 18 in which the cell inner frame 101 is fitted is placed on the column part 712 of the sample cup placing stand 71 with the cup end surface 181 disposed on the lower side.

Figure 25A:
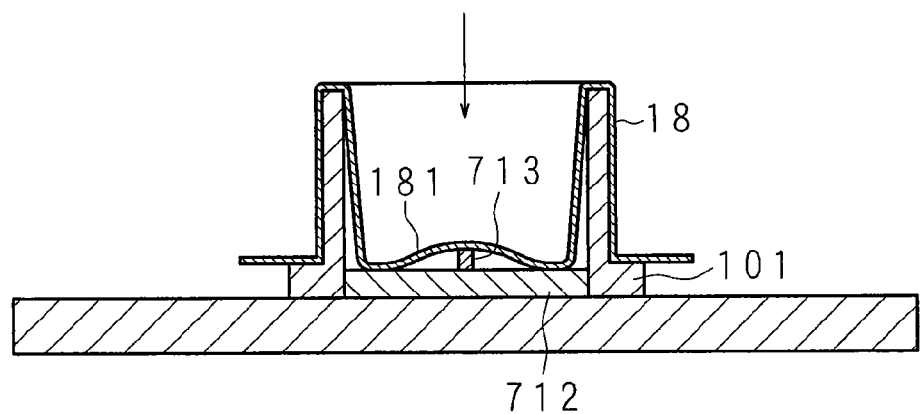
FIGS. 25A and 25B are explanatory views for explaining the method for assembling the sample cell when viewed from the front side.
Figure 25B:
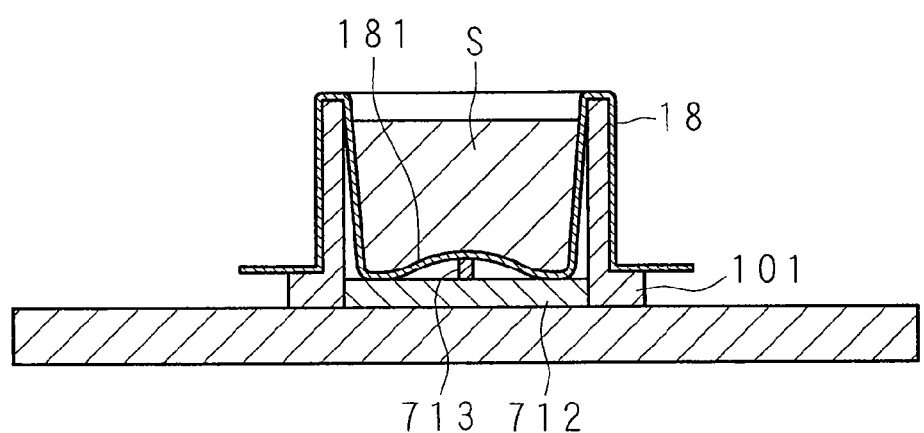

FIG. 25A is a cross-sectional view of the sample cup 18 placed on the sample cup placing stand 71. The column part 712 of the sample cup placing stand 71 is fitted in the cell inner frame 101, and the sample cup 18 is thereby positioned. In addition, the cup end surface 181 of the sample cup 18 is pushed by the projection part 713 to be convexly deformed inwardly of the sample cup 18. Next, as illustrated in FIG. 25A, the fluid sample S is injected into the sample cup 18. FIG. 25B is a cross-sectional view of the sample cup 18 after the fluid sample S is injected thereinto. The fluid sample S is injected up to the level slightly lower than the upper end of the sample cup 18 in order to prevent the fluid sample S from overflowing from the sample cup 18.

Figure 26A:
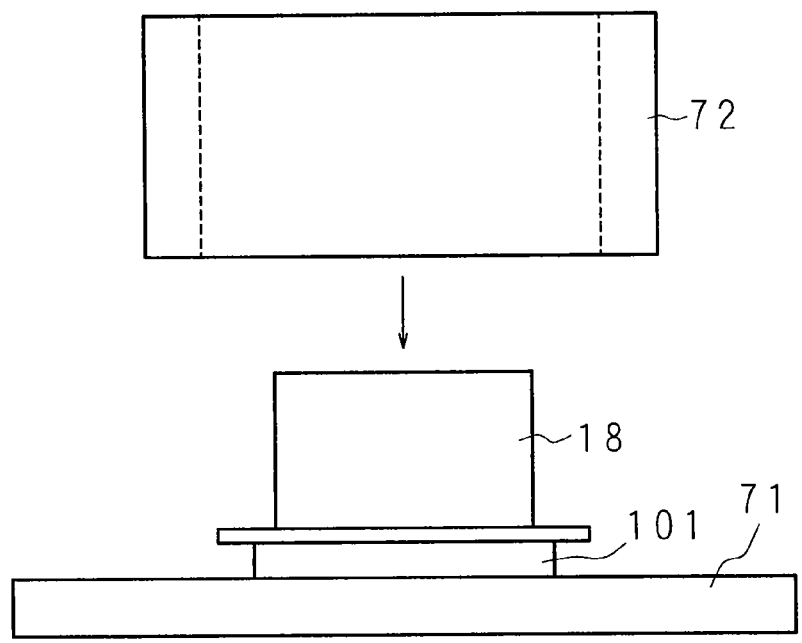
FIGS. 26A and 26B are explanatory views for explaining the method for assembling the sample cell when viewed from the front side.
Figure 26B:
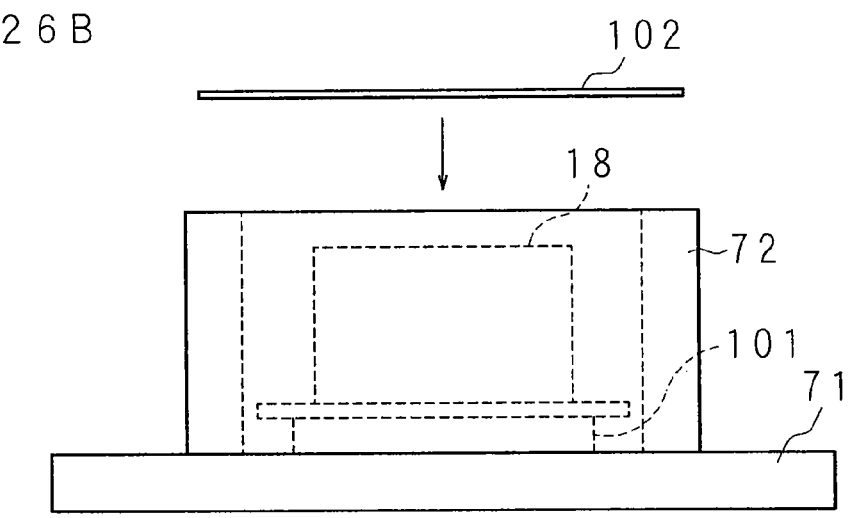

After the fluid sample S is injected, as illustrated in FIG. 26A, the sheet placing instrument 72 is placed on the sample cup placing stand 71 so as to cover the sample cup 18 from above. In FIG. 26A, the inner surface of the sheet placing instrument 72 is indicated by broken lines, In the state where the sheet placing instrument 72 is placed on the sample cup placing stand 71, the sample cup 18 is surrounded by the sheet placing instrument 72 and, as illustrated in FIG. 26B, the sample cup 18 is covered with the sheet placing instrument 72 when viewed from the front side. In FIG. 26B, the inner surface of the sheet placing instrument 72, and the sample cup 18 and the cell inner frame 101 that are covered with the sheet placing instrument 72 are indicated by broken lines. It is to be noted that the fluid sample S may also be injected into the sample cup 18 after the sheet placing instrument 72 is placed on the sample cup placing stand 71. Subsequently, as illustrated in FIG. 26B, the X-ray transmission sheet 102 is placed on the sheet placing instrument 72. In this state, since the X-ray transmission sheet 102 is placed on the sheet placing instrument 72 higher than the sample cup 18, the X-ray transmission sheet 102 does not come in contact with the fluid sample S inside the sample cup 18.

Figure 27A:
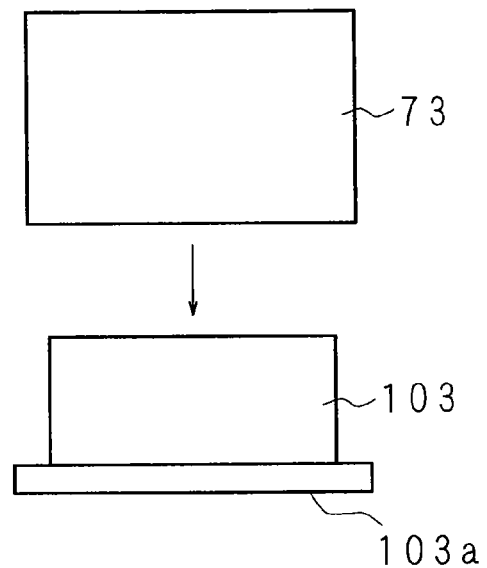
FIGS. 27A and 27B are explanatory views for explaining the method for assembling the sample cell when viewed from the front side.
Figure 27B:
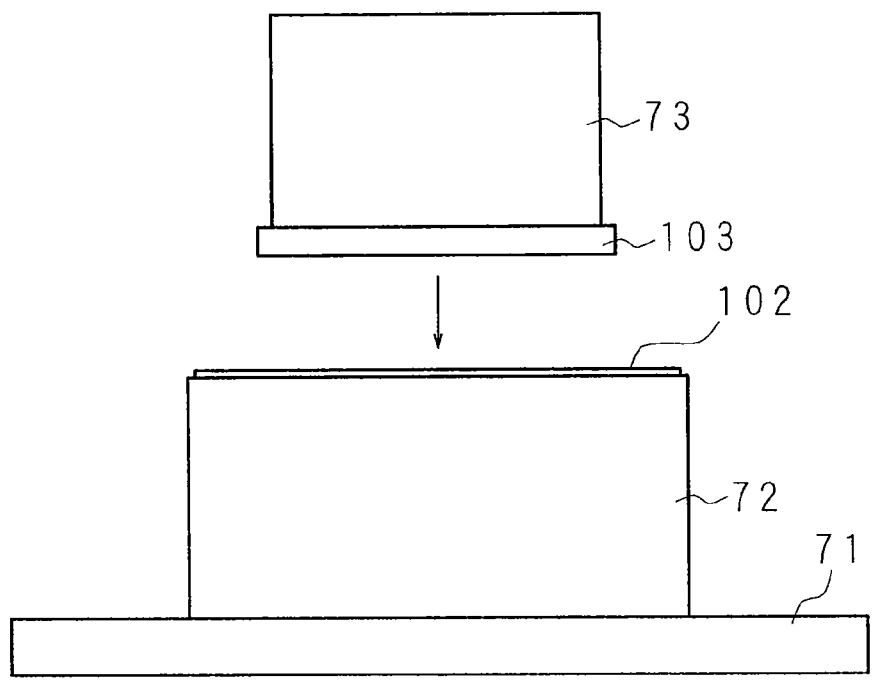

Further, as illustrated in FIG. 27A, the outer frame fitting instrument 73 is put from above on the cell outer frame 103 with the flange part 103a disposed on the lower side. In this state, the cell outer frame 103 is fitted in the outer frame fitting instrument 73. Next, as illustrated in FIG. 27B, the outer frame fitting instrument 73 in which the cell outer frame 103 is fitted is pushed from above onto the sample cup placing stand 71 on which the X-ray transmission sheet 102 is placed. The cell outer frame 103 is pushed in by the outer frame fitting instrument 73 while being guided by an inner wall of the sheet placing instrument 72. The X-ray transmission sheet 102 is pushed by the cell outer frame 103 to come in contact with the rim of the opening portion of the sample cup 18. The cell outer frame 103 is moved downward with the X-ray transmission sheet 102 interposed between itself and the sample cup 18, and is stopped at the point where the projection part 103b is engaged with the groove part 101b of the cell inner frame 101.

Figure 28A:
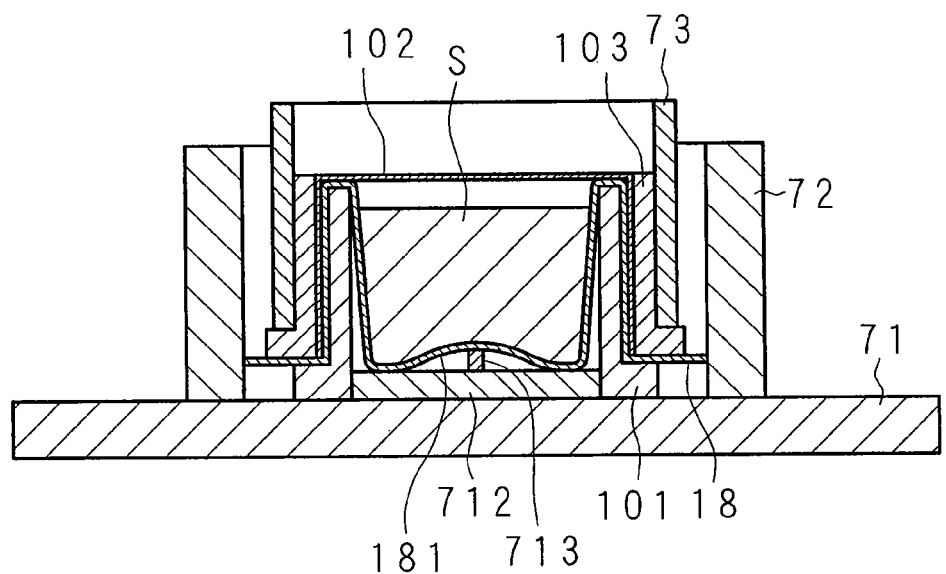
FIGS. 28A and 28B are explanatory views for explaining the method for assembling the sample cell when viewed from the front side.

FIG. 28A is a cross-sectional view illustrating the state where the cell outer frame 103 is pushed in. The cell outer frame 103 is externally fitted on the cell inner frame 101 with the sample cup 18 and the X-ray transmission sheet 102 interposed therebetween, and the sample cup 18 and the X-ray transmission sheet 102 are held between the cell inner frame 101 and the cell outer frame 103. In addition, the X-ray transmission sheet 102 pushed by the cell outer frame 103 to be moved downward covers and closes the opening portion of the sample cup 18. When the cell outer frame 103 is pushed in, the X-ray transmission sheet 102 is pulled in a radial direction, and the cell outer frame 103 is guided by the inner wall of the sheet placing instrument 72 and the outer frame fitting instrument 73 to be pushed in substantially vertically so that the tension pulling the X-ray transmission sheet 102 in the radial direction becomes uniform. Consequently, a cockle is unlikely to occur in the X-ray transmission sheet 102, and the X-ray transmission sheet 102 is disposed in tension so as to seal the sample cup 18. Moreover, since the X-ray transmission sheet 102 does not come in contact with the fluid sample S or the rim of the opening portion of the sample cup 18 until immediately before the X-ray transmission sheet 102 is disposed in tension, when the X-ray transmission sheet 102 is disposed in tension, the occurrence of the cockle due to the adhesion of the fluid sample S to the X-ray transmission sheet 102 before the completion of assembly of the sample cell 1 is prevented. Furthermore, when the cell outer frame 103 is pushed in, the entire sample cell 1 is pushed downward, and the cup end surface 181 is thereby deformed reliably by the projection part 713 of the sample cup placing stand 71. Since the height of the outer frame fitting instrument 73 is higher than that of the cell outer frame 103, even when the cell outer frame 103 is fitted on the sample cup 18, the upper end of the outer frame fitting instrument 73 projects above the upper end of the sheet placing instrument 72, and it is possible to reliably push in the cell outer frame 103 by pushing the outer frame fitting instrument 73 from above.

Figure 28B:
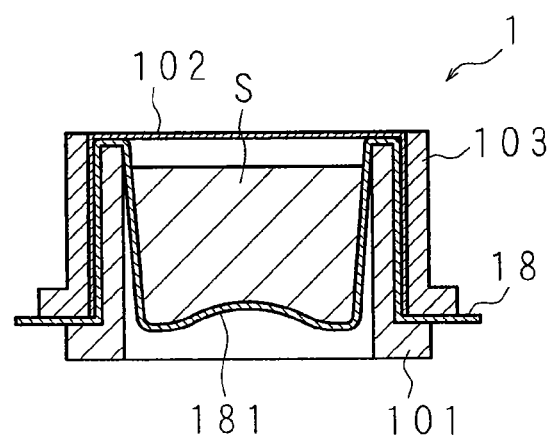

Next, the outer frame fitting instrument 73 and the sheet placing instrument 72 are removed, and the sample cell 1 is detached from the sample cup placing stand 71, whereby the assembly of the sample cell 1 illustrated in the cross-sectional view of FIG. 28B is completed. Since the upper end of the outer frame fitting instrument 73 projects above the upper end of the sheet placing instrument 72, it is easy to remove the outer frame fitting instrument 73. The assembled sample cell 1 has the fluid sample S enclosed thereinside, and the cup end surface 181 is convexly deformed inwardly.

Figure 29:
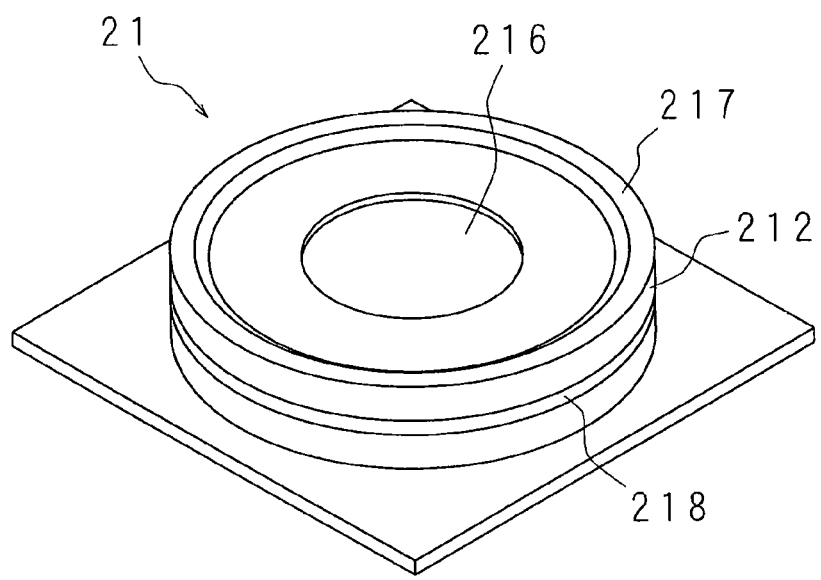
FIG. 29 is a perspective view of a cell supporting member that is turned upside down.

Subsequently, a description will be given of a cell holder assembly instrument for assembling the cell holder 20, and a method for assembling the cell holder 20 by using the cell holder assembly instrument. The cell holder 20 is assembled by turning the cell supporting member 21 upside down, and then attaching the X-ray transmission sheet 22 thereto. FIG. 29 is a perspective view of the cell supporting member 21 that has been turned upside down. The cell supporting member 21 has an annular bottom surface 217 corresponding to a back surface of the bottom plate part 213, and a wall surface of the circumferential wall part 212 is formed with a circling groove 218 that is provided completely around the circumference of the opening portion 216. The assembly of the cell holder 20 only requires adjustment of the X-ray transmission sheet 22 so as to close the opening portion 216, and fixing of the X-ray transmission sheet 22 by fitting an annular elastic member such as an O ring or the like in the circling groove 218. However, because the cockle tends to occur in the X-ray transmission sheet 22 when the X-ray transmission sheet 22 is fixed using the annular elastic member such as the O ring or the like, the cell holder assembly instrument capable of attaching the X-ray transmission sheet 22 to the cell supporting member 21 while preventing the occurrence of the cockle is required.

Figure 30:
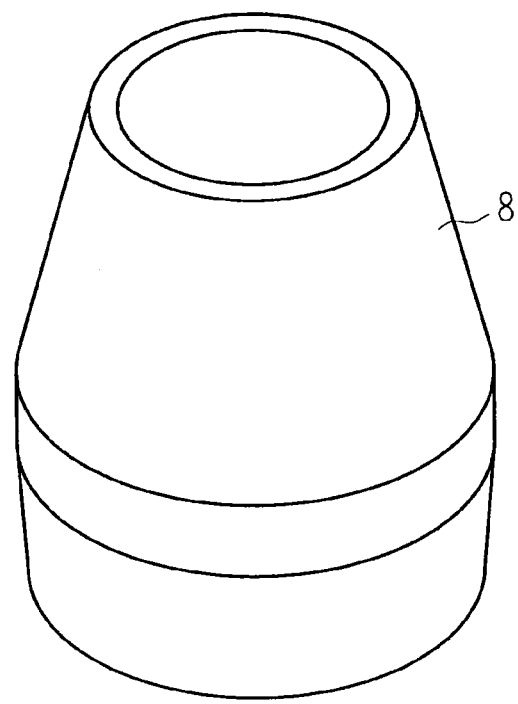
FIG. 30 is a perspective view illustrating a cell holder assembly instrument for assembling the cell holder.

FIG. 30 is a perspective view illustrating the cell holder assembly instrument for assembling the cell holder 20. A cell holder assembly instrument 8 is formed into a cylindrical shape as a whole with a material such as a metal, a resin, or the like. In addition, the cell holder assembly instrument 8 is formed into a tapered shape that monotonously reduces in outer diameter from a halfway point in an axial direction toward its top surface. Further, the cell holder assembly instrument 8 is formed into a tapered shape that monotonously reduces in outer diameter from a halfway point in the axial direction toward its bottom surface. That is, the outer diameter of the cell holder assembly instrument 8 is gradually increased from the top surface toward the bottom surface and, after the outer diameter reaches the maximum value, the outer diameter is gradually reduced from a halfway point. FIG. 31 is a cross-sectional view of the cell holder assembly instrument 8 taken along the axis thereof. In a circumferential edge portion of a bottom surface 81 of the cell holder assembly instrument 8, formed is an annular projection part 82 projecting in a direction orthogonal to the bottom surface 81. The inner diameter of the annular projection part 82 is a size that allows the cell holder assembly instrument 8 to be externally fitted on the circumferential wall part 212 of the cell supporting member 21. In addition, the height of the annular projection part 82 is smaller than a distance from the bottom surface 217 to the circling groove 218 of the cell supporting member 21.

Figure 32A:
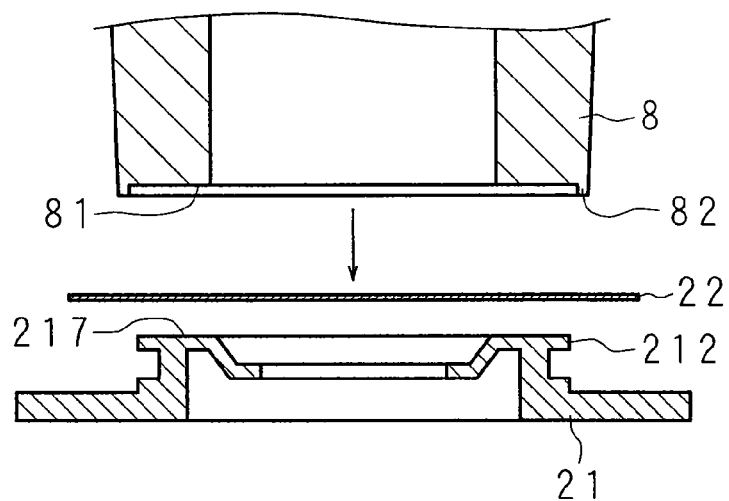
FIGS. 32A and 32B are schematic cross-sectional views for explaining a method for assembling the cell holder using the cell holder assembly instrument.
Figure 32B:
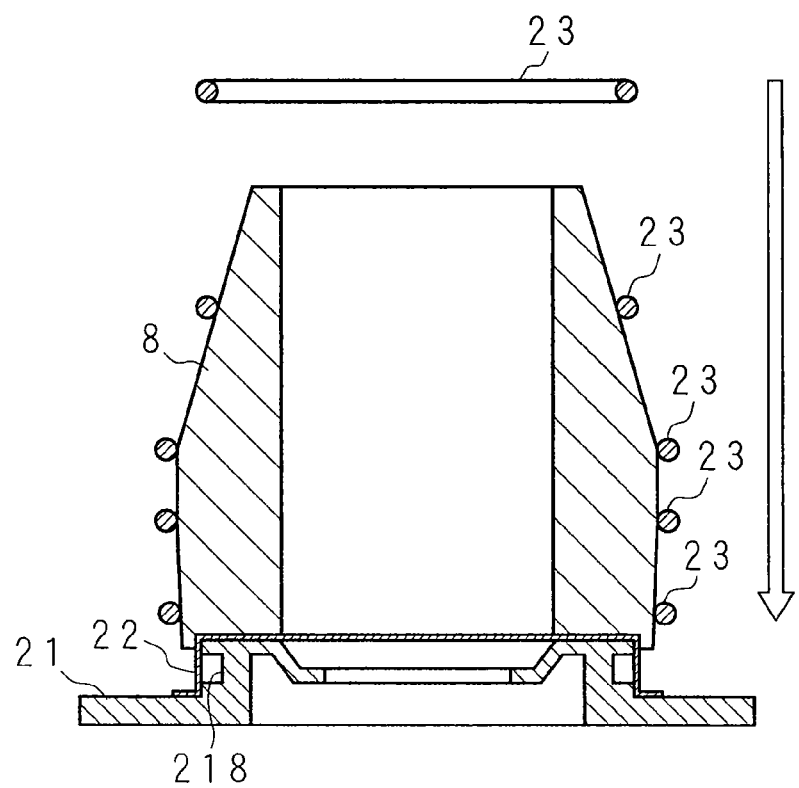

FIGS. 32A and 32B are schematic cross-sectional views for explaining the method for assembling the cell holder 20 by using the cell holder assembly instrument 8. First, as illustrated in FIG. 32A, the X-ray transmission sheet 22 is placed on the bottom surface 217 of the cell supporting member 21 with the bottom surface 217 disposed on the upper side, and the cell holder assembly instrument 8 is further placed on the X-ray transmission sheet 22. In the state where the cell holder assembly instrument 8 is placed, the bottom surface 81 of the cell holder assembly instrument 8 is in contact with the bottom surface 217 of the cell supporting member 21 with the X-ray transmission sheet 22 interposed therebetween. In addition, the annular projection part 82 is externally fitted on the circumferential wall part 212 of the cell supporting member 21 with the X-ray transmission sheet 22 interposed therebetween.

In the state where the cell holder assembly instrument 8 is placed on the cell supporting member 21, an O ring 23 is put on the cell holder assembly instrument 8 from the side of the top surface. The diameter of the O ring 23 is a size that allows the O ring 23 to be fitted in the circling groove 218 of the cell supporting member 21. Next, as indicated by an open arrow in FIG. 32B, the O ring 23 is gradually moved from the side of the top surface toward the bottom surface 81. Because the top surface of the cell holder assembly instrument 8 has the smallest outer diameter, and the outer diameter is increased as the O ring 23 is moved, the O ring is uniformly widened. Moreover, the O ring 23 is further moved to be lower than the annular projection part 82. Since the outer diameter of the cell holder assembly instrument 8 is gradually reduced from the halfway point, the O ring 23 is easily moved with its elasticity. In addition, since the annular projection part 82 is externally fitted on the circumferential wall part 212 of the cell supporting member 21, the O ring 23 is reliably moved to the cell supporting member 21 from the cell holder assembly instrument 8 by being moved continuously. The O ring 23 is further moved downward along the circumferential wall part 212, and the O ring 23 is thereby fitted in the circling groove 218 of the cell supporting member 21 to fix the X-ray transmission sheet 22 to the cell supporting member 21. Thereafter, by removing the cell holder assembly instrument 8, the assembly of the cell holder 20 is completed.

FIG. 33 is a cross-sectional view illustrating the assembled cell holder 20. The X-ray transmission sheet 22 placed on the bottom surface 217 of the cell supporting member 21 is fixed by the O ring 23 fitted in the circling groove 218. When the O ring 23 is moved along the circumferential wall part 212, the X-ray transmission sheet 22 is uniformly pulled in the radial direction, and is disposed in tension so as to close the opening portion 216.

Figure 34:
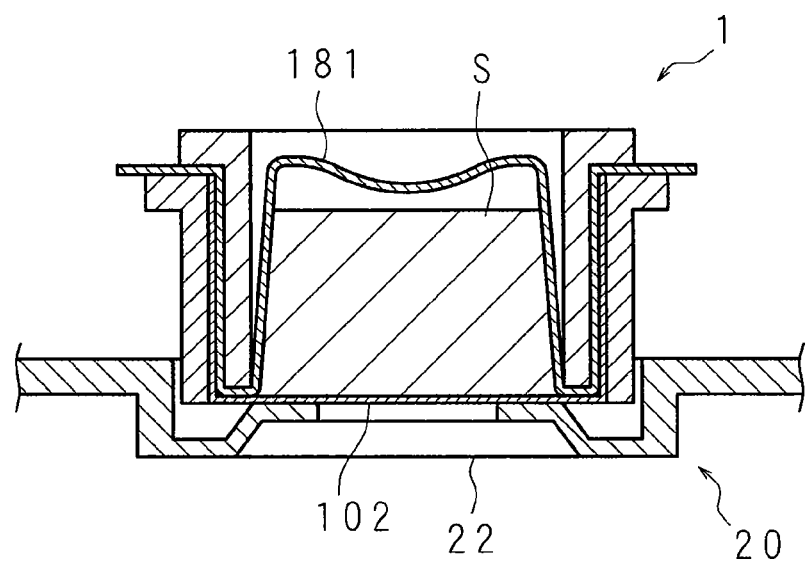
FIG. 34 is a cross-sectional view illustrating the sample cell placed on the cell holder.

The assembled cell holder 20 is turned upside down and, with the X-ray transmission sheet 22 disposed on the lower side, the cell holder 20 is attached to the opening portion of the housing 5 using a bolt or the like. By attaching the cell holder 20, the measurement chamber 51 of the fluorescent X-ray analyzer is sealed. Further, the assembled sample cell 1 is turned upside down, and is placed on the cell holder 20 with the X-ray transmission sheet 102 serving as the bottom surface and the cup end surface 181 disposed on the upper side. FIG. 34 is a cross-sectional view illustrating the sample cell 1 placed on the cell holder 20. The sample cell 1 is placed on the cell holder 20 such that the X-ray transmission sheet 102 serves as the bottom surface, and the X-ray transmission sheet 102 comes in contact with the supporting plane 215 of the cell supporting member 21. The fluid sample S and a small amount of air are enclosed inside the sample cell 1. With the sample cell 1 placed on the cell holder 20, the primary X-rays are emitted from the X-ray tube 3, and the fluorescent X-ray analysis is performed. The primary X-rays from the X-ray tube 3 are emitted from the lower side in the drawing illustrated in FIG. 34, the primary X-rays are transmitted through the X-ray transmission sheets 22 and 102 to be emitted to the fluid sample S inside the sample cell 1, and the fluorescent X-rays generated from the fluid sample S are transmitted through the X-ray transmission sheets 102 and 22 to be emitted.

Figure 35:
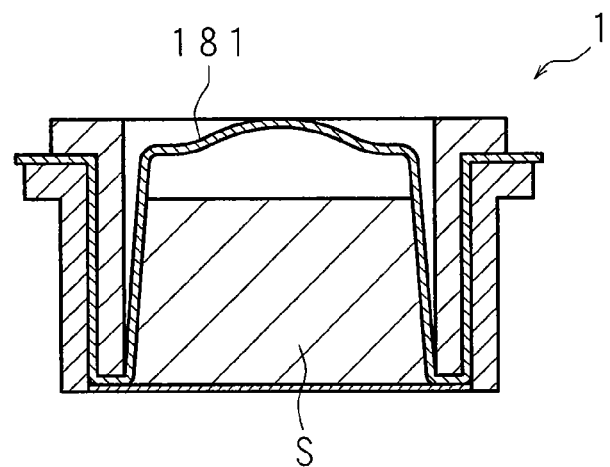
FIG. 35 is a cross-sectional view illustrating the sample cell after the cup end surface is deformed in response to an increase in pressure.

When the fluid sample S is volatilized with the passage of time to increase the internal pressure of the sample cell 1 during the execution of the fluorescent X-ray analysis, the cup end surface 181 is deformed in response to the increase in pressure. FIG. 35 is a cross-sectional view illustrating the sample cell 1 after the cup end surface 181 is deformed in response to the increase in pressure. The cup end surface 181 that has been convexly deformed inwardly in advance is deformed while being expanded outwardly of the sample cell 1 in response to the increase in the internal pressure of the sample cell 1, and the internal capacity of the sample cell 1 is thereby increased. The internal capacity of the sample cell 1 is increased to relieve the increase in the internal pressure of the sample cell 1, and hence the expansion of the X-ray transmission sheet 102 due to the increase in pressure is prevented.

As has been described above, in the fluorescent X-ray analyzer using the sample cell 1 assembled by using the sample cell assembly instrument of Embodiment 2, even when the fluid sample S is volatilized inside the sample cell 1 to increase the internal pressure of the sample cell 1, the X-ray transmission sheet 102 as the window part through which the primary X-rays and the fluorescent X-rays are transmitted is not expanded. Since the X-ray transmission sheet 102 that allows transmission of the fluorescent X-rays is not expanded, the distance between the fluid sample S and the X-ray detector 4 detecting the fluorescent X-rays is not fluctuated, and the intensities of the fluorescent X-rays detected by the X-ray detector 4 are not fluctuated as well. Consequently, the intensities of the fluorescent X-rays are not changed by factors other than the element distribution in the fluid sample S, and hence it becomes possible to perform the element analysis of the fluid sample S by the fluorescent X-ray analysis with high precision.

In addition, in Embodiment 2, the occurrence of the cockle in the X-ray transmission sheet 102 due to the adhesion of the fluid sample S to the X-ray transmission sheet 102 before the completion of assembly of the sample cell 1, and due to the nonuniformity in tension pulling the X-ray transmission sheet 102 when the cell outer frame 103 is fitted is prevented. Consequently, the occurrence of the cockle in the X-ray transmission sheet 102 does not cause the leakage of the fluid sample S from the sample cell 1. Furthermore, the distance between the fluid sample S and the X-ray detector 4 is not fluctuated by the cockle in the X-ray transmission sheet 102, and hence it becomes possible to perform the element analysis of the fluid sample S by the fluorescent X-ray analysis with high precision.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A sample cell assembly instrument used when a sample cell for fluorescent X-ray analysis is assembled by containing a sample in a sample cup, sealing an opening portion of the sample cup in which the sample is contained with an X-ray transmission sheet, and fitting an outer frame on the sample cup with the X-ray transmission sheet interposed therebetween, comprising:

a sample cup placing stand for placing the sample cup thereon;

wherein the sample cup placing stand has a positioning part positioning the sample cup when the sample cup with the opening portion disposed on an upper side is placed, and a pushing-up part pushing up an end surface disposed on a lower side of the sample cup to convexly deform the end surface inwardly of the sample cup when the outer frame is fitted on the placed sample cup from above, a cylindrical inner frame is fitted in the sample cup on a side of the end surface thereof and an end portion of the cylindrical inner frame projects above the end surface, the positioning part is provided on a flat surface of the sample cup placing stand and has an upper surface that is raised from the flat surface at a height, the positioning part having a shape for positioning the cylindrical inner frame, and the pushing-up part is a projection projecting from the upper surface of the positioning part and is provided in a center of the positioning part.

2. The sample cell assembly instrument of claim 1, wherein the positioning part is a column, an outer diameter of the column is a size that allows the column to be fitted in the cylindrical inner frame, and the upper surface of the positioning part defines the height of the column, the height of the column being smaller than a distance from the end portion of the cylindrical inner frame to the end surface.

3. The sample cell assembly instrument of claim 1, further comprising:

a sheet placing instrument that is separate from the sample cup placing stand, has a tubular shape, has both end surfaces in parallel with each other and orthogonal to an axis, has an inner diameter larger than an outer diameter of the sample cell, has a height when placed on the sample cup placing stand higher than the sample cup, is placed on the sample cup placing stand so as to surround the sample cup, and is used in order to place the X-ray transmission sheet thereon.

4. The sample cell assembly instrument of claim 3, further comprising:

an outer frame fitting instrument that is separate from the sample cup placing stand and the sheet placing instrument, has a tubular shape, has an inner diameter allowing the outer frame to be fitted therein, has an outer diameter smaller than the inner diameter of the sheet placing instrument, has a height higher than the outer frame, and is used in order to push the outer frame fitted therein toward the sample cup from an upper side of the X-ray transmission sheet placed on the sheet placing instrument to fit the outer frame on the sample cup.

* * * * *